US012741049B2

(12) United States Patent
Subramanian et al.

(10) Patent No.: US 12,741,049 B2
(45) Date of Patent: Sep. 22, 2026

(54) PHOTOCATALYTIC AND PHOTO(ELECTRO)CATALYTIC APPROACHES FOR VIRAL DECONTAMINATION

(71) Applicant: Nevada Research & Innovation Corporation, Reno, NV (US)

(72) Inventors: Vaidyanathan Subramanian, Reno, NV (US); Subhash C. Verma, Reno, NV (US)

(73) Assignee: Nevada Research & Innovation Corporation, Reno, NV (US)

( * ) Notice: Subject to any disclaimer, the term of this patent is extended or adjusted under 35 U.S.C. 154(b) by 623 days.

(21) Appl. No.: 18/015,461

(22) PCT Filed: Jul. 15, 2021

(86) PCT No.: PCT/US2021/041873
§ 371 (c)(1),
(2) Date: Jan. 10, 2023

(87) PCT Pub. No.: WO2022/016006
PCT Pub. Date: Jan. 20, 2022

(65) Prior Publication Data
US 2023/0277716 A1 Sep. 7, 2023

Related U.S. Application Data

(60) Provisional application No. 63/053,254, filed on Jul. 17, 2020.

(51) Int. Cl.
*A61L 9/20* (2006.01)
*B01J 21/06* (2006.01)
(Continued)

(52) U.S. Cl.
CPC ............ *A61L 9/205* (2013.01); *B01J 21/063* (2013.01); *B01J 23/06* (2013.01); *B01J 23/18* (2013.01);
(Continued)

(58) Field of Classification Search
CPC ............ A61L 9/205; B01J 35/45; B01J 35/49
See application file for complete search history.

(56) References Cited

U.S. PATENT DOCUMENTS 7,541,509 B2 * 6/2009 Sigmund ................ B01J 21/185 588/299
2005/0224360 A1 10/2005 Varghese et al.
(Continued)

FOREIGN PATENT DOCUMENTS

CN 2639766 Y * 9/2004
CN 101873886 A * 10/2010 ........... B01D 53/323
KR 20140075971 A * 6/2014 ............. B01J 35/45

OTHER PUBLICATIONS

English translation of CN-2639766-Y (Year: 2004).*
(Continued)

*Primary Examiner* — Sean E Conley

(57) ABSTRACT

Disclosed herein are systems and methods for decontaminating surfaces from human coronaviruses, such as SARS coronavirus 2 (SARS-CoV-2), and structures for decontamination from human coronaviruses. A structure for decontamination includes a first surface and a decontamination layer on the first surface. The decontamination layer comprises a nanostructured photocatalyst. Human coronaviruses on the decontamination layer are exposed to UV radiation and/or visible light. After the exposure, the human coronaviruses on the decontamination layer are inactivated. In some embodiments, the decontamination layer can include
(Continued)

additives and/or an electrical bias can be applied to further reduce the exposure time required for viral inactivation.

9 Claims, 12 Drawing Sheets

Specification includes a Sequence Listing.

(51) Int. Cl.

| | |
|---|---|
| ***B01J 23/06*** | (2006.01) |
| ***B01J 23/18*** | (2006.01) |
| ***B01J 35/39*** | (2024.01) |
| ***B01J 35/45*** | (2024.01) |

(52) U.S. Cl.

CPC ............... *B01J 35/39* (2024.01); *B01J 35/45* (2024.01); *A61L 2209/16* (2013.01); *A61L 2209/21* (2013.01)

(56) References Cited

U.S. PATENT DOCUMENTS

| | | | |
|---|---|---|---|
| 2013/0150809 | A1 | 6/2013 | Whiteford et al. |
| 2014/0027288 | A1 | 1/2014 | Nyberg et al. |
| 2018/0204977 | A1 | 7/2018 | Dheeraj et al. |

OTHER PUBLICATIONS

English Translation CN-101873886-A (Year: 2010).*

English translation of KR-20140075971-A (Year: 2014).*

International Search Report and Written Opinion issued for International Application No. PCT/US2021/041873 on Dec. 7, 2021.

Harini et al., “Enhanced visible light photocatalytic performance of sulphur doped nano bismuth titanate semiconductor,” *Materials Research Express*, 6(7): 1-4, Apr. 24, 2019.

Simmons et al., “Disinfection of pulsed xenon ultraviolet irradiation on SARS-CoV-2 and implications for environmental risk of COVID-19 transmission,” *MedRxiv*, posted May 11, 2020.

* cited by examiner

PHOTOCATALYTIC AND PHOTO(ELECTRO)CATALYTIC APPROACHES FOR VIRAL DECONTAMINATION

CROSS REFERENCE TO RELATED APPLICATION

This is the U.S. National Stage of International Application No. PCT/US2021/041873, filed Jul. 15, 2021, which application claims the benefit of the earlier filing date of U.S. Provisional Patent Application No. 63/053,254, filed on Jul. 17, 2020, the entirety of which is incorporated herein by reference.

FIELD

The present disclosure relates generally to viral decontamination, and more particularly, to photocatalytic and photo(electro)catalytic approaches to decontaminate surfaces from human coronaviruses, such as severe acute respiratory syndrome (SARS) coronavirus 2 (SARS-CoV-2).

BACKGROUND

The novel SARS-CoV-2, also known as human coronavirus 2019 (hCoV-19), is the causative agent of the pneumonia-like coronavirus disease 2019 (COVID-19). As of June 2020, SARS-CoV-2 had infected more than 8.5 million people globally, including over 2 million people in the United States. Dissemination of the virus can occur via multiple modes, including contact with respiratory droplets generated by an infected subject and contact with surfaces contaminated with the virus. The stability of SARS-CoV-2 on such surfaces may be a factor in its wide-spread dissemination within the human population despite adoption of aggressive mitigation measures, such as physical distancing protocols, that have been implemented by numerous countries. Indeed, SARS-CoV-2 has been shown to be stable on smooth surfaces for up to 72 hours. Moreover, respiratory droplets (e.g., on the order of 10 μm) carrying the virus can easily circulate in the air and be deposited on surfaces remote from the infected subject.

Surfaces contaminated with SARS-CoV-2 can be periodically cleaned using various chemical agents (e.g., hydrogen peroxide, bleach, or other disinfectants recognized by the Environmental Protection Agency (EPA)). However, it may be unsafe for humans to be exposed to such chemicals, thereby requiring protective gear during the cleaning process. Alternatively, exposure with ultraviolet (UV) radiation (e.g., UVA, UVB, and/or UVC) has previously been used to disinfect surfaces, for example, in public transportation systems. However, the efficacy of UV irradiation on surface decontamination is not well established. In addition, it may be required to maintain the chemical application or the UV exposure for several minutes in order to provide sufficient removal of the virus, and the chemical or UV exposure offers little to no protection against the virus between applications. Given the highly-contagious, potentially-lethal nature of SARS-CoV-2 and the lack of an available vaccine, there remains an urgent need to effectively decontaminate surfaces, in a short period of time (e.g., on the order of a minute or less) or continuously, in order to mitigate the further spread of the virus.

Embodiments of the disclosed subject matter may address one or more of the above-noted problems and disadvantages, among other things.

SUMMARY

Embodiments of the disclosed subject matter provide systems and methods for decontaminating surfaces from human coronaviruses, such as SARS coronavirus 2 (SARS-CoV-2), as well as structures to be decontaminated from such human coronaviruses. In some embodiments, a surface of the structure to be decontaminated can be provided with a decontamination layer that includes a particulate film-based and/or nanostructured photocatalyst. The decontamination layer can be exposed to electromagnetic radiation, for example, wavelengths in the ultra-violet (UV) and/or visible range. In particular embodiments, the electromagnetic radiation synergistically interacts with the nanostructured photocatalyst to destroy, or at least inactivate, all, or substantially all (e.g., at least 80%, and preferably at least 99%), human coronaviruses in contact with the decontamination layer. In some embodiments, this activity can be accomplished within one minute or less. The electromagnetic radiation exposure can be periodic or continuous, and may be provided from a separate dedicated illumination source (e.g., UV lamp or light-emitting diode) or a pre-existing source (e.g., UV or visible radiation from a halogen lamp, incandescent bulb, or fluorescent lamp already used for indoor lighting, or from solar radiation in an outdoor location). In some embodiments, the electromagnetic radiation exposure time effective to destroy the coronavirus can be reduced by modifying the decontamination layer with one or more additives, such as a light harvesting material or a conductive particle, and/or by simultaneously (or substantially simultaneously) subjecting the decontamination layer to an electrical bias.

In some embodiments, the surface upon which the decontamination layer is provided can be one available for touching by a subject, for example, the surface of a three-dimensional object, such as a table, desk, counter, chair, bed, toilet, wall, door, handle, flooring, railing, or the like. In other embodiments, the surface can be part of a decontamination device arranged such that human coronaviruses circulating in the air are incident on the decontamination layer. In such embodiments, the decontamination device can be an air handling device, such as an air purifier or disinfection unit of a heating, ventilation, and air-conditioning (HVAC) system.

In one representative embodiment, a decontamination method for human coronavirus is disclosed and comprises exposing the human coronavirus and a decontamination layer in contact with the human coronavirus to UV radiation and/or visible light. The decontamination layer can comprise a nanostructured photocatalyst.

In another representative embodiment, a structure for decontamination can comprise a first surface and a decontamination layer on the first surface. The decontamination layer can comprise a nanostructured photocatalyst. In some embodiments, the structure further comprises a human coronavirus in contact with the decontamination layer.

The foregoing and other objects and features of the present disclosure will become more apparent from the following detailed description, which proceeds with reference to the accompanying figures.

BRIEF DESCRIPTION OF THE DRAWINGS

Embodiments will hereinafter be described with reference to the accompanying drawings, which have not necessarily been drawn to scale. Where applicable, some elements may be simplified or otherwise not illustrated in order to assist in the illustration and description of underlying features. For example, in some figures, the propagation of light has not been shown or has been illustrated using block arrows or dashed lines rather than employing ray diagrams. Throughout the figures, like reference numerals denote like elements.

FIG. 7A is a graph of copies of hCoV-NL63 detected in the setup of FIG. 6 after different ultraviolet (UV) radiation exposure times without any decontamination layer.

FIG. 7B is a graph of active copies of hCoV-NL63 collected from the setup of FIG. 6 and used for infection of HEK293L cells after different UV radiation exposure times without any decontamination layer.

FIG. 8 is a graph of active copies of hCoV-NL63 collected from the setup of FIG. 6 after different UV radiation exposure times (i) without any decontamination layer and (ii) with a decontamination layer of $TiO_2$ nanoparticles (TNPs).

FIG. 9 shows immunofluorescence assay images of a monolayer of HEK293L cells infected by copies of hCoV-NL63 for different decontamination parameters, with panel A showing a positive control of infection by hCoV-NL63 without being subject to any decontamination; panel E showing a negative control of uninfected HEK293L cells; panels B-D showing infection by hCoV-NL63 after 1, 5, and 10 minute exposures to UV radiation, respectively, without any decontamination layer; and panels F-H showing infection by hCoV-NL63 after 1, 5, and 10 minutes exposures to UV radiation, respectively, with a decontamination layer of TNPs.

SEQUENCES

Figure 1A:
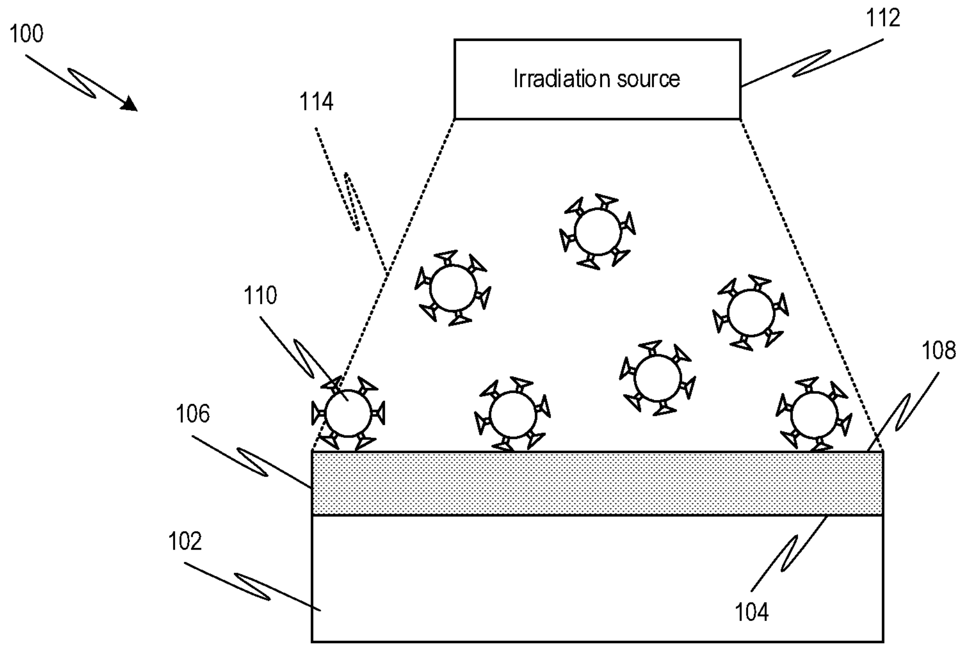
FIG. 1A is a simplified side view illustrating aspects of a catalytic approach for viral decontamination of a photocatalyst-coated surface, according to one or more embodiments of the disclosed subject matter.

The nucleic and amino acid sequences listed in the accompanying sequence listing are shown using standard letter abbreviations for nucleotide bases, and three letter code for amino acids, as defined in 37 C.F.R. § 1.822. Only one strand of each nucleic acid sequence is shown, but the complementary strand 5 is understood as included by any reference to the displayed strand. The Sequence Listing is submitted as an ASCII text file in the form of the file named "Sequence.txt" (~0.785 kb), which was created on Jul. 14, 2021, which is incorporated by reference herein. In the accompanying sequence listing:

SEQ ID NO: 1 is an NL63-S forward primer.

SEQ ID NO: 2 is an NL63-S reverse primer.

DETAILED DESCRIPTION

Overview of Terms

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, structures, and systems are not limited to any specific aspect or feature or combination thereof, nor do the disclosed embodiments require that any one or more specific advantages be present, or problems be solved. The technologies from any example can be combined with the technologies described in any one or more of the other examples. In view of the many possible embodiments to which the principles of the disclosed technology may be applied, it should be recognized that the illustrated embodiments are only illustrative examples and should not be taken as limiting the scope of the disclosed technology.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

Unless explained otherwise, all technical and scientific terms used herein have the same meaning as commonly understood to one of ordinary skill in the art to which this disclosure belongs. Although methods and compounds similar or equivalent to those described herein can be used in the practice or testing of the present disclosure, suitable methods and compounds are described below. The compounds, methods, and examples are illustrative only and not intended to be limiting, unless otherwise indicated.

As used in this application and in the claims, the singular forms "a," "an," and "the" include the plural forms unless the context clearly dictates otherwise. Additionally, the terms "have" or "includes" means "comprises." The term "or" refers to a single element of stated alternative elements or a combination of two or more elements, unless the context clearly indicates otherwise.

Any numerical range described herein will be understood to include the endpoints and all values between the endpoints. Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

The following explanations of specific terms and abbreviations are provided to facilitate the description of various aspects of the disclosed subject matter and to guide those of ordinary skill in the art in the practice of the disclosed subject matter:

Decontamination Layer: A layer (or plurality of layers) comprised of a nanostructured photocatalyst and formed on a surface that would otherwise be exposed to human coronavirus and/or surrogates thereof.

Electrical Bias: An applied direct current (DC) voltage. In some embodiments, for example, the DC voltage can be in a range of ±0.1-1 $V_{DC}$. Any power source can be used to supply the DC voltage, such as but not limited to, a battery, a photovoltaic panel, and an electrical-grid-based power outlet in combination with a suitable AC-DC converter or DC power supply.

Electrically-Conductive Material: A material that increases an electrical conductivity of the nanostructured photocatalyst or a surface upon which the nanostructured photocatalyst is disposed. The electrically-conductive additive can also enhance reduction-oxidation (redox) properties of the nanostructured photocatalyst.

Human Coronavirus (hCoV): Includes, but is not limited to, severe acute respiratory syndrome (SARS) coronavirus 2 (SARS-CoV-2), also known as human coronavirus 2019 (hCoV-19), as well as testing surrogates thereof, such as human coronavirus NL63 (hCoV-NL63), human coronavirus OC43 (HCoV-OC43), and human coronavirus 229E (hCoV-229E).

Light Harvesting Material: A material that absorbs electromagnetic radiation at wavelengths different from that of the nanostructured photocatalyst and thereby increases photocurrent upon exposure. Generally, the light harvesting material can extend an effective wavelength range for operation of the nanostructured photocatalyst. In some embodiments, bismuth titanate is used to extend UV-absorbance of the nanostructured photocatalyst into the visible light portion of the electromagnetic spectrum.

Nanoparticles (NP): A material particle that has three orthogonal dimensions in the nanoscale regime (e.g., between 0.1 nm and 100 nm) and can be considered a zero-dimensional (0-D) material.

Nanostructured Photocatalyst: A material formed as nanometer-scale structure, such as nanoparticles, nanotubes, nanorods, and/or nanowires, and having properties that cause acceleration and/or enhancement of a photochemical reaction by creation of electron-hole pairs upon exposure to appropriate electromagnetic irradiation. In some embodiments, for example, the photocatalyst can have a bandgap of 3 eV or greater.

Nanorod (NR) or Nanowire (NW): A nanometer-scale structure that has a narrow rod-like shape with a closed core. Generally, the nanowire can have a diameter (perpendicular to the cylindrical axis) of 100 nm or less and a ratio of the diameter to length (parallel to the cylindrical axis) that is at least 1:100, for example, greater than 1:1000, and the nanorod can have a diameter (perpendicular to the cylindrical axis) of 100 nm or less and a ratio of the diameter to length (parallel to the cylindrical axis) that is less than 1:100. Thus, the nanowire and nanorod can be considered 1-D materials.

Nanotube (NA): A nanometer-scale structure that has a narrow cylindrical shape with the material forming an outer circumferential wall that extends along a cylindrical axis and defines an open core. Generally, the nanotube can have a diameter (perpendicular to the cylindrical axis) of 100 nm or less, and a ratio of the diameter to length (parallel to the cylindrical axis) of the nanotube can be at least 1:100, for example, greater than 1:1000. Thus, the nanotube can be considered a one-dimensional (1-D) material. Exemplary fabrication techniques for nanotube embodiments disclosed herein can include, but are not limited to, wet chemical techniques (e.g., sol-gel chemistry) and anodization.

Subject: A human or other animal, such as a domesticated animal, capable of being infected by and/or spreading the human coronaviruses.

Touch Surface: A surface that is often touched by, or at least available for occasional contact with, a subject and that can support viable human coronaviruses thereon absent decontamination. Examples include, but are not limited to, surfaces of a three-dimensional object, such as a table, desk, counter, chair, bed, toilet, wall, door, handle, flooring, railing, or the like.

Ultraviolet (UV) Radiation: Electromagnetic radiation having wavelengths in the range of 10 nm-400 nm. UVA radiation has wavelengths in the range of 315 nm-400 nm. UVB radiation has wavelengths in the range of 280 nm-315 nm. UVC radiation has wavelengths in the range of 100 nm-280 nm.

Ultraviolet-visible (UV-vis) Radiation: Electromagnetic radiation having wavelengths in a range that spans the UV regime (10 nm-400 nm) and the visible regime (380 nm-740 nm).

Viral Inactivation: Sufficient degradation of the human coronavirus that prevents the virus from infecting human cells.

Introduction

Embodiments of the disclosed subject matter provide systems and methods for decontaminating surfaces from human coronaviruses and structures for decontamination of severe acute respiratory syndrome (SARS) coronavirus 2 (SARS-CoV-2) and surrogates thereof. Also disclosed are structures for decontamination. In some such embodiments, a surface of the disclosed structure is provided with a decontamination layer that includes a nanostructured photocatalyst. In some embodiments of the disclosed method, the decontamination layer is exposed to electromagnetic radiation, for example, wavelengths in the ultra-violet (UV) and/or visible range, such embodiments also being referred to herein as methods using a photocatalytic approach. The electromagnetic radiation synergistically interacts with the nanostructured photocatalyst to destroy, or at least inactivate, substantially all human coronaviruses (hCoV) in contact with the decontamination layer, for example, within one minute or less. The electromagnetic radiation exposure can be periodic or continuous, and may be provided from a separate, dedicated illumination source (e.g., UV light-emitting diode) or a pre-existing source (e.g., UV or visible radiation from a halogen lamp, incandescent bulb, or fluorescent lamp already used for indoor lighting, or from solar radiation in an indoor or outdoor location).

In some embodiments, the time used for viral inactivation can be further reduced by modifying the decontamination layer with one or more additives, such as a light harvesting material or an electrically-conductive material, and/or by subjecting the decontamination layer to an electrical bias (such embodiments also being referred to herein as methods using a photo(electro)catalytic approach). The light harvesting material can also absorb electromagnetic radiation at wavelengths different from that absorbed by the nanostructured photocatalyst, thereby enhancing absorption of radiation by the decontamination layer.

In some embodiments, the decontamination layer can be grown, deposited, painted, coated, applied, or otherwise provided on a surface of a structure susceptible to or exposed to viral contamination. Structures can include, but are not limited to, films, foils, mesh, wires, and the like. The surface can be used as-is prior to deposition of the decontamination layer, or it can be pre-treated before deposition. For example, the constituent materials of the decontamination layer (e.g., the nanostructured photocatalyst and any other additives, such as light-harvesting materials and/or conductive particles) can be combined with appropriate binders to form an emulsion, which can be sprayed onto a surface to form the decontamination layer thereon. In some embodiments, existing device(s) (e.g., commercially-available spray painting tools) and/or technique(s) can be used to apply the emulsion onto a surface to form the decontamination layer thereon.

In some embodiments, the decontamination layer is provided on a touch surface, such as the surface of a table, desk, chair, door, handle, wall, ceiling, flooring, or railing. In other embodiments, the decontamination layer is part of an air-handling unit designed to inactivate hCoV circulating in the air, for example, by contacting the circulating hCoV with the decontamination layer and exposing to electromagnetic radiation. For example, the air-handling unit can be constructed as a stand-alone air purifier or a decontamination module of a heating, ventilation, and air-conditioning system.

Structure Embodiments

Figure 1B:
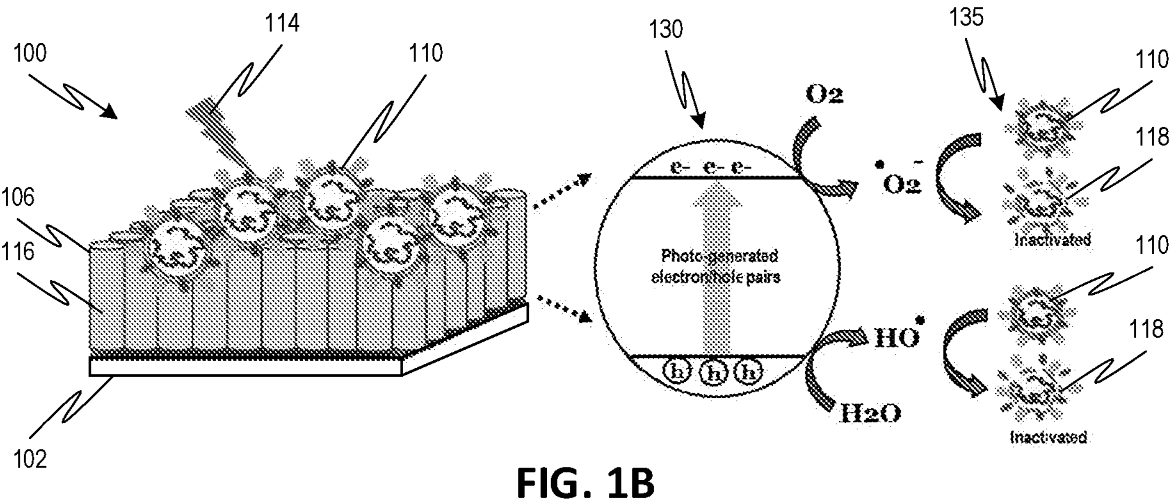
FIG. 1B illustrates a theoretical mechanism for viral inactivation using a nanotubular photocatalyst, according to one or more embodiments of the disclosed subject matter.

FIGS. 1A-1B illustrate an exemplary configuration 100 for viral decontamination using a nanostructured photocatalyst. A structure 102, susceptible to surface contamination with hCoV 110 (e.g., SARS-CoV-2 or surrogates thereof), is provided with a decontamination layer 106, which is comprised of a nanostructured photocatalyst (for example, nanotubes 116 in FIG. 1B). A pre-existing or separately-provided radiation source 112 emits electromagnetic radiation 114 that is incident on decontamination layer 106 and hCoV 110. For example, the radiation 114 may be ultra-violet (UV) radiation and/or visible light. The nanostructured photocatalyst of the decontamination layer 106 absorbs the electromagnetic radiation 114 and operates synergistically with the radiation 114 to inactivate the hCoV 110 in contact therewith.

In particular, as shown in panel 130 of FIG. 1B, the exposure to radiation 114 generates electron-hole pairs ($e^-$ and $h^+$) in the nanostructure 116 of the decontamination layer 106. The electron-hole pair generation, in turn, produces strong oxidizing species (e.g., reactive oxygen species), for example, hydroxyl and superoxide radicals from adsorbed water molecules on the surface of the nanostructure 116. The holes can catalyze oxidation processes and can convert water/hydroxide molecules to peroxide/hydroxyl radicals, while the electrons can induce reduction reactions and react with molecular oxygen to generate the superoxide radicals. As shown in panel 135 of FIG. 1B, these radicals can interact with hCoV 110 in contact with the decontamination layer 106 to transform hCoV 110 into an inactivated form 118. In particular, the oxidizing species generated by the nanostructures 116 upon exposure to radiation 114 can attack and destroy (via oxidative damage) the organic protein shell of hCoV 110, thereby rendering the hCoV 110 incapable of infecting a subject.

In some embodiments, all (or substantially all; e.g., at least 80%, and preferably at least 99%) hCoV 110 in contact with the decontamination layer 106 can be rendered inactive in under five minutes, and preferably within one minute or less (e.g., 20 seconds to 60 seconds, such as 30 seconds to 60 seconds, or 40 seconds to 60 seconds, or 50 seconds to 60 seconds, or 20 seconds, 30 seconds, 40 seconds, 50 seconds, or 60 seconds). The time period for inactivation is measured from when the virus 110 is both in contact with decontamination layer 106 and exposed to radiation 114. Thus, in embodiments where decontamination layer 106 is continuously exposed to radiation 114 from source 112, the inactivation time may be measured from when hCoV 110 first comes into contact with decontamination layer 106. Alternatively or additionally, where decontamination layer 106 is intermittently exposed to radiation 114 from source 112 (e.g., for periodic decontamination of the structure 102), the inactivation time may be measured from initiation of radiation exposure.

In some embodiments, the radiation source 112 can be an existing interior lighting source, such as a halogen lamp, incandescent bulb, or fluorescent lamp, with appropriate intensity that is used to illuminate an area around or in a vicinity of structure 102. In addition to visible wavelengths, such interior lighting sources may also emit radiation in the entire UV regime (e.g., UVA, UVB, and UVC), which radiation can be absorbed by the decontamination layer 106 to inactivate the virus. Alternatively or additionally, the radiation source 112 can be separate from any existing interior lighting source and can have a radiation output tailored to the decontamination layer. For example, the radiation source 112 can be a wavelength-selected radiation source, such as a UV lamp, laser, laser diode, or light-emitting diode (LED). Alternatively or additionally, the radiation 114 can be natural solar radiation, for example, in an outdoor environment or by sunlight directed into an interior space.

The decontamination layer 106 can be provided directly on and in contact with a target surface 104 of the structure 102 or on the target surface 104 with one or more intervening layers between the decontamination layer 106 and the target surface 104, for example, to improve adhesion of the decontamination layer 106 to the structure 102 and/or increase electrical conductivity. The structure 102 can be any type of physical structure where target surface 104 would otherwise be available for touch by a subject, such as but not limited to a table, desk, chair, door, handle, wall, ceiling, flooring, or railing. Although illustrated as substantially planar, the structure 102 and/or target surface 104 can have any type of geometry or configuration.

In some embodiments, the nanostructured photocatalyst can have a bandgap of 3 eV or greater, for example, between 3 eV and 4.5 eV, and the electromagnetic radiation 114 comprises UV radiation. For example, the nanostructured photocatalyst can be one or more of titanium oxide ($TiO_2$) nanoparticles (TNP), nanorods (TNR), or nanotubes (TNT); zinc oxide (ZnO) nanoparticles (ZNP), nanorods (ZNR), or nanotubes (ZNA); strontium titanate ($SrTiO_3$) nanoparticles (SNP), nanorods (SNR), or nanotubes (SNA); or silicon nanowires (SiNW). TNP, TNR, or TNT have a bandgap of ~3.2 eV; ZNP, ZNR, or ZNA have a bandgap of ~3.1 eV to 3.4 eV; SNP, SNR, or SNA have a bandgap of ~3.25 eV; and SiNW have a bandgap of ~2.5 eV or greater (depending on geometry and material composition). In general, the 1-D nanostructures (e.g., TNT, TNR, ZNA, ZNR, SNA, SNR, and SiNW) may be more effective than 0-D nanostructures (e.g., TNP, ZNP, and SNP), for example, due to better separation of charges during radiation exposure and more effective and production of oxidizing species. The nanostructured photocatalysts can be capable of inactivating hCoV in contact therewith using relatively low-intensity exposures, e.g., 0.01 $mW/cm^2$ of UVA radiation.

In some embodiments, the decontamination layer can be modified to further include one or more additives. On type of additive is a light harvesting material that can be added to the decontamination layer to improve photocatalytic properties thereof. The light harvesting material can promote charge separation in the nanostructures and/or absorb electromagnetic radiation at wavelengths different from that of the photocatalyst. In some embodiments, the light harvesting material comprises metal nanoparticles (e.g., transition or post-transition metal nanoparticles) incorporated into the nanostructured photocatalyst, or at least in combination with the photocatalyst in the decontamination layer. For example, the light harvesting material can comprise bismuth titanate ($Bi_{12}TiO_{20}$), which can increase the stability of the photocatalyst (e.g., to inhibit corrosion), enhance the overall light absorbance (e.g., enhance absorbance of wavelengths up to 400 nm and thus extending into the visible regime of the electromagnetic spectrum), and/or boost photocurrent (which is a measure of photocatalytic activity).

Another type of additive is an electrically-conductive material that can be added to the decontamination layer (e.g., decontamination layer 106), or provided as an intervening layer between the structure surface and the decontamination layer (e.g., structure surface 104 and decontamination layer 106). The electrically-conductive material can increase the electrical conductivity of the structure and/or the decontamination layer (e.g., structure 102 and/or the decontamination layer 106), for example, to enhance redox properties of the photocatalyst and/or absorption of radiation (e.g., radiation 114). In some embodiments, the electrically-conductive material comprises a conductive carbon material, such as graphene, graphene oxide, graphene quantum dots, or graphitic carbon nitride ($g\text{-}C_3N_4$). For example, the electrically-conductive material can comprise reduced graphene oxide (RGO) and/or tin oxide doped with a halogen, such as fluorine.

Alternatively or additionally, a direct current (DC) electric field can be applied to the decontamination layer and/or the structure to enhance the photocatalytic properties of the nanostructured photocatalyst. For example, the electric field may have a magnitude less than 1 $V_{DC}$, preferably 0.1 $V_{DC}$ to 0.5 $V_{DC}$. Such electric field applications can overcome the lack of electron-hole separation in oxide materials of the nanostructure photocatalyst by suppressing recombination among charged species, electrons, and holes therein. The inclusion of an electrically-conductive material (e.g., either in the decontamination layer 106 or as a separate layer in contact with the decontamination layer 106) can assist in the application of such electric fields.

Figure 2A:
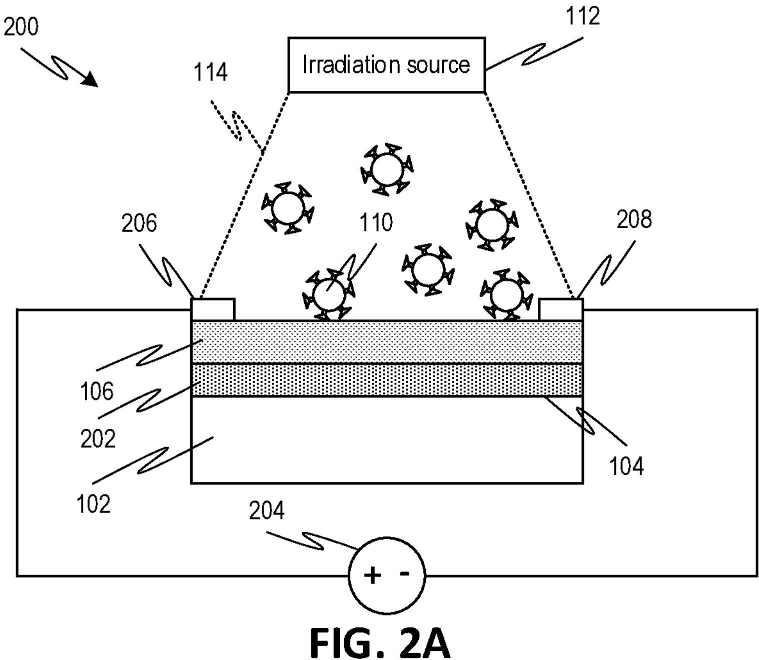
FIG. 2A is a simplified side view illustrating aspects of a photo(electro)catalytic approach for viral decontamination using a first exemplary electrode configuration for applying a voltage bias, according to one or more embodiments of the disclosed subject matter.

For example, FIG. 2A illustrates an exemplary configuration 200 employing a DC voltage bias for decontamination enhancement. In contrast to the configuration 100 of FIG. 1A, the structure 102 in FIG. 2A includes an electrically-conductive layer 202 (e.g., formed of conductive carbon or other electrically conductive material) on surface 104. The decontamination layer 106 can be provided on the electrically-conductive layer 202, although in other embodiments layers 106 and 202 can be combined together, for example, by incorporating electrically-conductive particles within the decontamination layer 106. One or more electrodes 206, 208 can be disposed in contact with the decontamination layer 106, and a DC voltage source 204 can apply an electric field to the decontamination layer 106 and/or the structure 102 via the electrodes 206, 208.

Figure 2B:
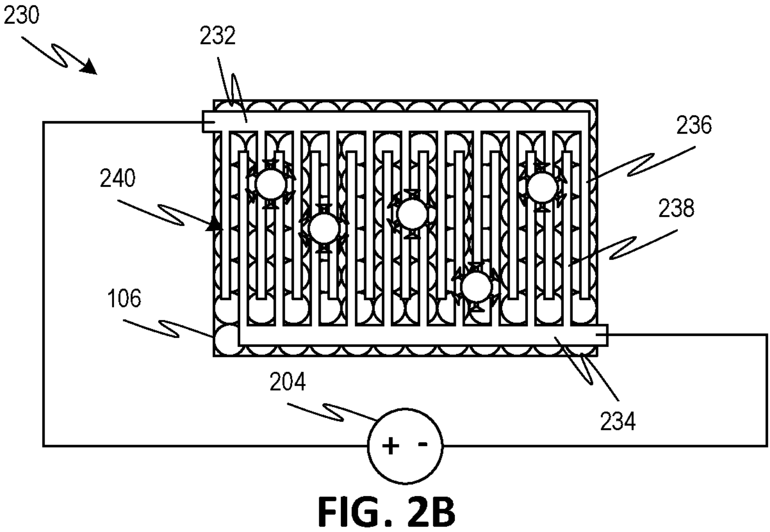
FIG. 2B is a simplified plan view illustrating aspects of a photo(electro)catalytic approach for viral decontamination using a second exemplary electrode configuration for applying a voltage bias, according to one or more embodiments of the disclosed subject matter.

Other configurations for applying an electrical field to the decontamination layer 106 and/or the structure 102 are also possible according to one or more contemplated embodiments. For example, FIG. 2B illustrates another exemplary configuration 230 that employs an interdigitated electrode array 240 (also referred to as a comb-finger array) to apply a DC electric field from voltage source 204 to the decontamination layer 106. The electrode array 240 can be formed by a positive electrode 232 with a plurality of first fingers 236 extending therefrom and a negative electrode 234 with a plurality of second fingers 238 extending therefrom. The first fingers 236 and the second fingers 238 can be alternately disposed with each other, such that each first finger 236 is disposed between a pair of adjacent second fingers 238, and vice versa (except for fingers at the end of the array 240). The electrode array 240 can be disposed on the decontamination layer 106 (e.g., on a surface exposed to hCoV 110), under the decontamination layer 106 (e.g., between the structure surface 104 and the decontamination layer 106), or within the decontamination layer 106 (e.g., with the nanostructured photocatalyst being disposed in the gaps between fingers 236, 238 and electrodes 232, 234).

Figure 2C:
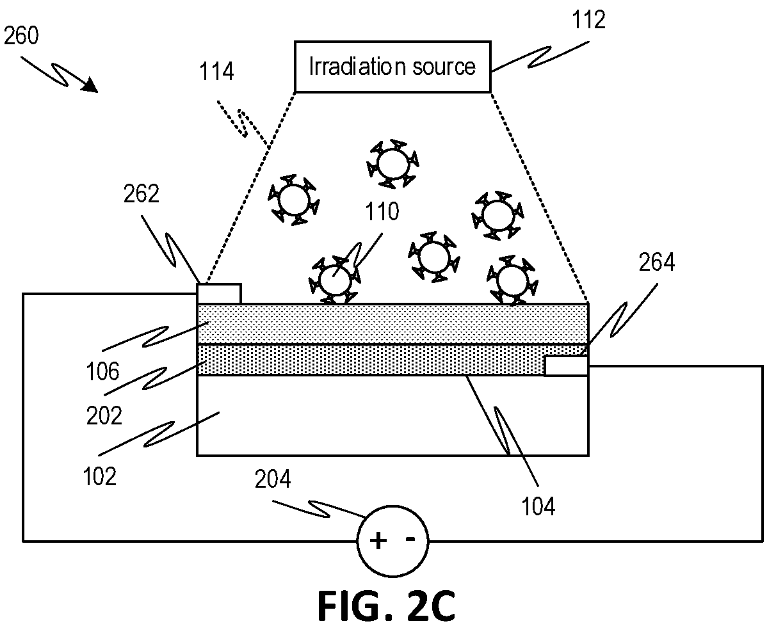
FIG. 2C is a simplified side view illustrating aspects of a photo(electro)catalytic approach for viral decontamination using a third exemplary electrode configuration for applying a voltage bias, according to one or more embodiments of the disclosed subject matter.

Alternatively or additionally, the electrodes can be in physical contact with a layer besides the decontamination layer 106. For example, FIG. 2C illustrates another exemplary configuration 260 that employs a first electrode 262 in contact with the decontamination layer 106 and a second electrode 264 in contact with electrically conductive layer 202. Using electrodes 262, 264, the DC voltage source 204 can apply an electric field to the decontamination layer 106 and/or structure 102. Other locations and configurations for the electrodes are also possible. For example, in some embodiments, the electrodes can be disposed on a surface of structure 102 with electrically conductive layer 202 provided thereover. In some embodiments, one of the electrodes can be embedded within the electrically conductive layer 202 or decontamination layer 106, and the other of the electrodes can be embedded within the electrically conducive layer 202 or decontamination layer 106.

Device Embodiments

Although the description above primarily focuses on decontamination of surfaces available for a subject to touch, embodiments of the disclosed subject matter are not limited thereto. Rather, in some embodiments, air with hCoV circulating therein can be decontaminated, for example, by bringing the hCoV from the air into contact with the decontamination layer and exposing to radiation. An air handling device can thus be provided with the decontamination layer and one or more appropriate radiation sources designed to expose the decontamination to appropriate radiation. The air handling device can also include structural features designed to displace the aerosol-based hCoV into contact with the decontamination layer, for example, curved or meandering flow paths (e.g., arcuate, serpentine, spiral or the like) and/or surface structures within the flowpath (e.g., baffles, spikes, mesh, or sponge structures that the air has to flow past or through). In some embodiments, the air handling device can be constructed as a standalone machine (e.g., an air purifier that extracts air from an enclosed space and returns decontaminated air to the space) or integrated with an existing heating, ventilation, or air-conditioning (HVAC) system (e.g., as a disinfection component or module within a duct or vent of the HVAC system).

Figure 5:
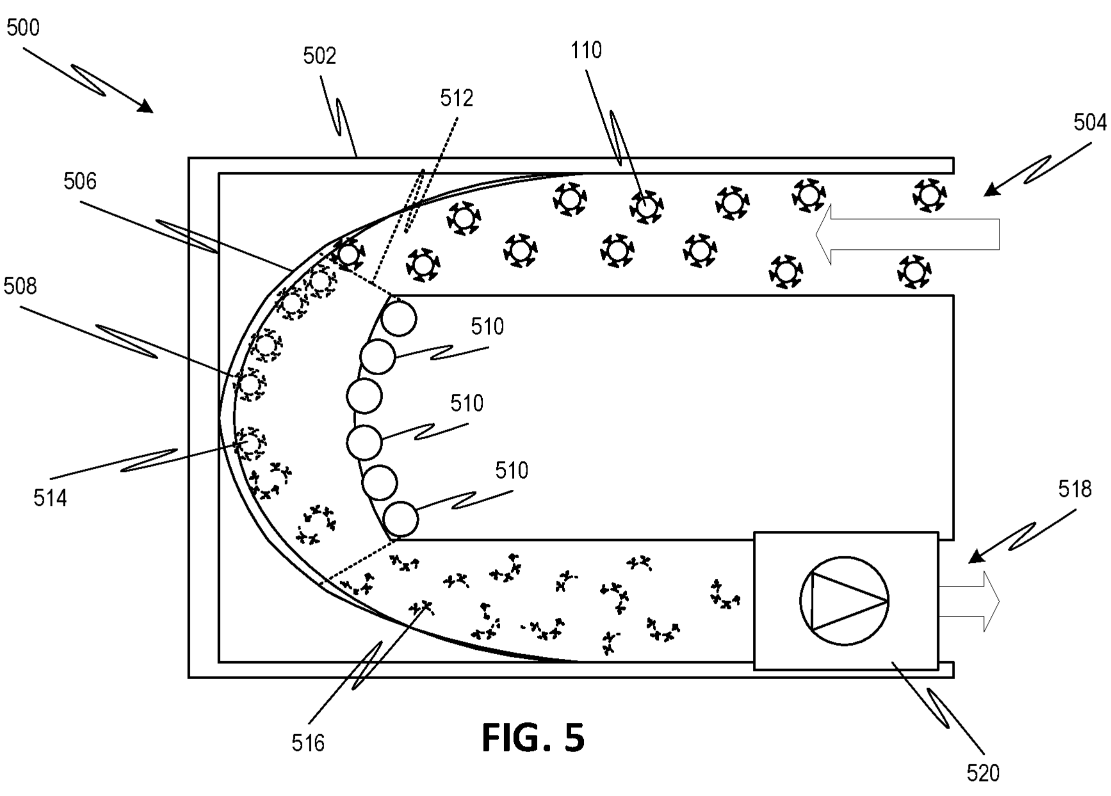
FIG. 5 is a simplified interior view illustrating aspects of an air-handling device employing the photocatalytic approach for viral decontamination, according to one or more embodiments of the disclosed subject matter.

For example, FIG. 5 illustrates an exemplary air handling device 500 for viral decontamination of circulating air. The air handling device 500 can have a housing 502 that defines an internal flow path between an inlet 504 and an outlet 518. An air mover 520 (e.g., a blower, fan, pump, or other air conveyance) causes air from the environment to enter through inlet 504, proceed along the internal flow path to an irradiation zone 512, and then exit the device 500 at outlet 518. Within irradiation zone 512, an internal surface 506 can have a decontamination layer 508 thereon. As described above, the decontamination layer 508 can be comprised of a nanostructured photocatalyst.

The internal surface 506 can be curved within the irradiation zone 512 such that hCoV 110 circulating within the air are urged toward and into contact with the decontamination layer 508. When hCoV 110 comes into contact with the decontamination layer 508 (for example, at contact point 514) and is exposed to radiation from one or more radiation sources 510 for a sufficient period of time, the integrity of the virus can be compromised and the virus subsequently inactivated (for example, inactivated form 516). For example, the length of the decontamination zone 512, the composition of the decontamination layer 508, the intensity of the radiation exposure, and/or the air speed along the internal flow path can be tailored such that a residence time of hCoV 110 within the decontamination zone 512 ensures that any hCoV therein will be inactivated. As noted above, the decontamination layer can include additives and/or a voltage bias can be applied to further reduce a radiation exposure times required for sufficient inactivation of the hCoV in contact with the decontamination layer 508.

Method of Making Embodiments

Figure 3:
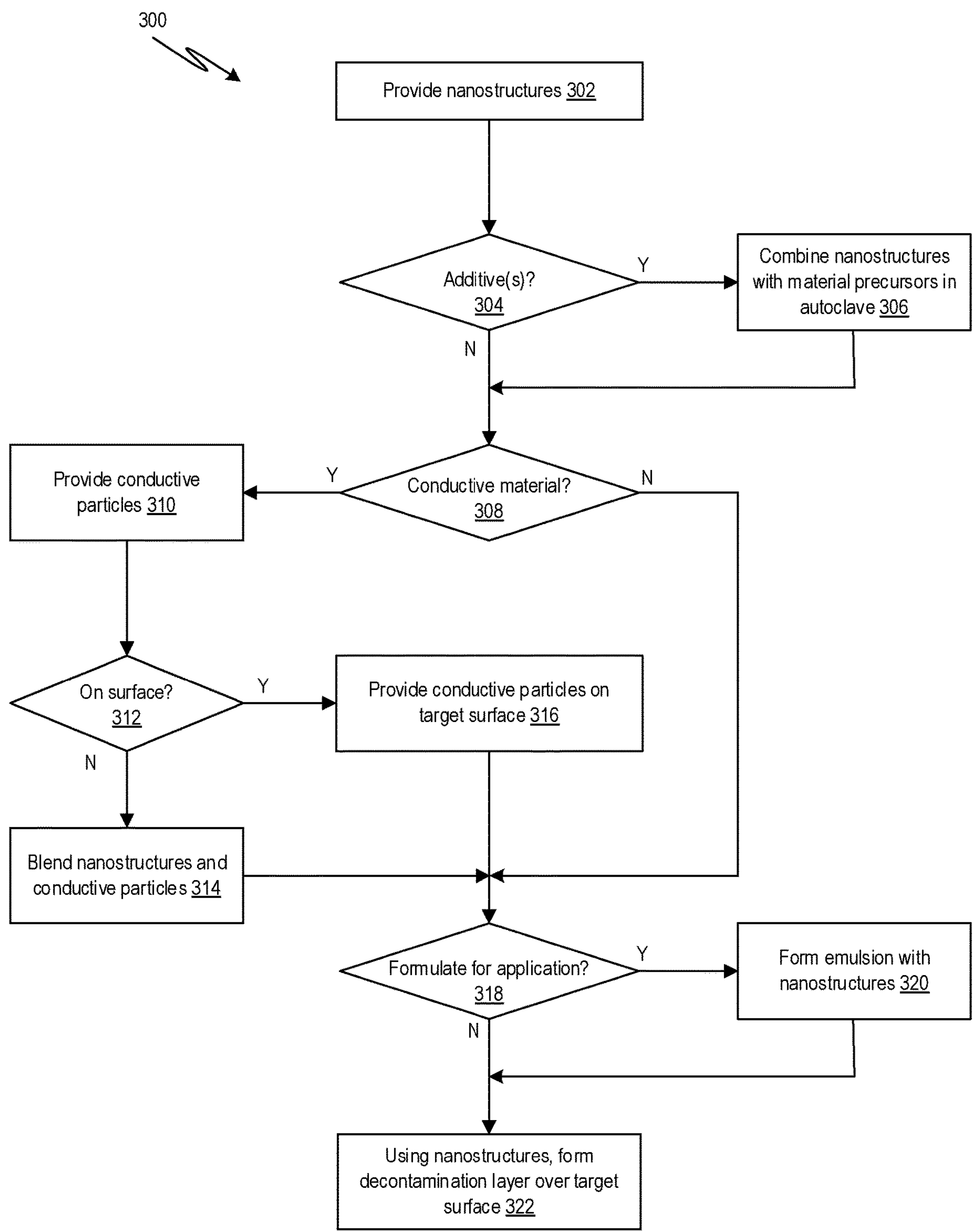
FIG. 3 is a process flow diagram for an exemplary fabrication method for forming a decontamination layer for use in the photocatalytic approach for viral decontamination, according to one or more embodiments of the disclosed subject matter.

FIG. 3 illustrates an exemplary method 300 for fabricating structures for photocatalytic decontamination. The method can initiate at process block 302, where one or more nanostructured photocatalysts (or composite including nanostructured photocatalysts) are provided. The nanostructured photocatalyst can have a bandgap of 3 eV or greater, for example, between 3 eV and 4.5 eV. For example, the nanostructured photocatalyst can be one or more of titanium oxide ($TiO_2$) nanoparticles (TNP), nanorods (TNR), or nanotubes (TNT); zinc oxide (ZnO) nanoparticles (ZNP), nanorods (ZNR), or nanotubes (ZNA); strontium titanate ($SrTiO_3$) nanoparticles (SNP), nanorods (SNR), or nanotubes (SNA); or silicon nanowires (SiNW). For example, the providing may include obtaining already-fabricated nanostructured photocatalysts from a commercial source and providing the photocatalysts in a suspension or other carrier medium for disposition on a target surface.

Alternatively or additionally, the nanostructured photocatalysts can be formed, for example, by growth on an appropriate substrate. For example, TNT can be formed by polishing titanium and then performing electrochemical anodization, such as described in Kar et al., "Improved Photocatalytic Degradation of Textile Dye Using Titanium Dioxide Nanotubes Formed over Titanium Wires," *Environ. Sci. Technol.,* 2009, 43: pp. 3260-65, the relevant portion of which is incorporated by reference herein. The composition of the electrolyte (e.g., acid medium) and anodization time (e.g., 20-60 minutes, such as 30 minutes to 60 minutes, or 40 minutes to 60 minutes, or 50 minutes to 60 minutes, or 20 minutes, 30 minutes, 40 minutes, 50 minutes, or 60 minutes), and/or voltage (e.g., 20V to 60V, such as 30V to 60V, or 40V to 60V, or 50V to 60V, or 20V, 30V, 40V, 50V, or 60V) can be varied to tune the resulting diameter and/or length of the TNT. In another example, ZNR can be prepared using a nucleation method, where zinc acetate is used as a precursor to nuclear on a glass slide followed by immersion in a zinc precursor solution to allow directional growth, such as described in Mukherjee et al., "A Unique Architecture Based on 1D Semiconductor, Reduced Graphene Oxide, and Chalcogenide with Multifunctional Properties," *Chem. Eur. J.,* 2014, 20: pp. 10456-65, the relevant portion of which is also incorporated by reference herein.

The method can proceed to decision block 304, where it is determined if a first additive should be added to the nanostructured photocatalyst, for example, to improve photocatalytic properties thereof. Such an additive can include, but are not limited to, a light harvesting material (and combinations of different light harvesting materials). If an additive is desired, the method can proceed from decision block 304 to process block 306, where the nanostructured photocatalyst is combined with the additive (e.g., light harvesting material or combination of light harvesting materials) in an autoclave and subject to a thermal treatment to integrate the additive with the nanostructured photocatalyst. In some embodiments, the light harvesting material can be bismuth titanate (e.g., $Bi_{12}TiO_{20}$) and the combination of nanostructured photocatalyst (e.g., TNT) and bismuth titanate can be formed using the procedure disclosed in U.S. Pat. No. 8,709,304, the relevant portion of which is incorporated by reference herein. For example, nanostructures prepared at process block 302 can subject to a thermal treatment under oxidative or reductive conditions and then added to an autoclave (e.g., a ceramic hydrothermal autoclave reactor lined with polytetrafluoroethylene (PTFE)) with bismuth precursor, a chelating agent, and pH adjustor. The contents of the autoclave are then thermally treated between 120° C. and 160° C., for 2-3 hours. Variations in the time and/or temperature can alter the size of the bismuth titanate nanoparticles and/or its deposition density on the nanostructure photocatalyst.

The two-stage fabrication process (separating formation of the nanostructured photocatalyst from subsequent formation of bismuth titanate nanoparticles) can allow for multiple variable control points, ease of scale-up, and product reproducibility between batches. In the formation of the nanostructures at 302, the variables that can be independently controlled include anodization conditions for TNT. If ZNR is used as the nanostructure material, the variables that can be independently controlled include seed mediated growth, electrolyte, additives, temperature, ramp rate, and atmosphere. In the formation of the light harvesting material at 306, the variables that can be independently controlled include bismuth precursor, titanium precursor, additives, temperature, pH, ramp rate, and atmosphere.

After completion of process block 306, or if first additive was not desired at decision block 304, the method can proceed to decision block 308, where it is determined if a different additive (e.g., an electrically conductive material) is desired, for example, to improve the electrical conductivity of the structure or the decontamination layer. If electrically conductive materials are desired, the method can proceed from decision block 308 to process block 310, where an electrically-conductive material is provided. For example, the electrically-conductive material can be a doped metal oxide layer, such as, fluorine-doped tin oxide. Alternatively or additionally, the electrically-conductive material can be a conductive carbon material, such as graphene, graphene oxide (e.g., reduced graphene oxide), or graphitic carbon nitride ($g\text{-}C_3N_4$). For example, the providing may include obtaining already-fabricated electrically-conductive particles from a commercial source. Alternatively or additionally, graphene oxide as the electrically-conductive material can be formed by Hummer's method, where potassium permanganate is added to a solution of graphite, sodium nitrate, and sulfuric acid. The graphene oxide can be thermally annealed under mild reduction conditions (e.g., in a nitrogen atmosphere at 300° C.-500° C.) to yield reduced graphene oxide (RGO). Further details regarding use of carbon-based materials can be found in Selvaraj et al., "How Beneficial Is Reduced Graphene Oxide (RGO) for Long-Term Photo Generated Charge Transport in Bismuth Titanate—RGO Nanocomposite Films?," *J. Electrochem. Soc.,* 2015, 163(2): pp. H147-H153, the relevant portion of which is incorporated by reference herein.

After completion of process block 310, the method can proceed to decision block 312, where it is determined if the electrically-conductive material should be added to the surface of the structure (e.g., as a separate intervening layer) or incorporated into the decontamination layer. When the structure is substantially non-conductive (e.g., glass), it may be desirable to provide the electrically-conductive particles directly on the structure surface. If it is decided to provide the electrically-conductive material on the surface of the structure, the method can proceed from decision block 312 to process block 316, where the electrically-conductive particles are provided on the target surface, for example, by depositing, coating, or otherwise applying thereon. Alternatively or additionally, if it is decided to provide the electrically-conductive material within the decontamination layer, the method can proceed from decision block 312 to process block 314, where the nanostructured photocatalyst (with or without light harvesting materials) is combined with the electrically-conductive material. For example, graphene oxide produced by Hummer's method can be blended with the nanostructured photocatalyst in a range of 1-2 wt. % and then thermally annealed under mild reduction conditions (e.g., in a nitrogen atmosphere at 300° C.-500° C.). For example, the result of process block 314 can be a composite of $TiO_2$+$Bi_{12}TiO_{20}$+RGO or ZnO+$Bi_{12}TiO_{20}$+RGO.

After completion of process block 314 or 316, or if conductive materials were not desired at decision block 308, the method can proceed to decision block 318, where it is determined if it is desired to formulate the nanostructured photocatalyst for application to the structure, for example, by incorporating the nanostructured photocatalyst in a paint or other emulsion for application to the target surface of the structure. If such formulation is desired, the method can proceed to process block 320, where the nanostructured photocatalyst is formulated for surface application. For example, the nanostructured photocatalyst can be combined with one or more inactive ingredients (e.g., binders) to form an emulsion. The inactive ingredients can include aqueous silica or alumina sols of various particle sizes and viscosities.

After completion of process block 320, or if formulation for application was not desired at decision block 318, the method can proceed to process block 322, where a decontamination layer including the nanostructured photocatalyst is formed over the target surface of the structure. When the nanostructured photocatalyst is incorporated into an emulsion via process block 320, the emulsion can be applied to the target surface using any conventional painting or coating techniques, such as but not limited to, spray painting, brush painting, roll painting, dip coating, spin coating, etc. Drying of the emulsion can result in the desired decontamination layer on the structure. In some cases, it may be desirable to provide a pre-coating on the structure surface prior to forming the decontamination layer, for example, to promote adhesion of the decontamination layer. For example, a coating of polyvinyl alcohol and/or polyethylene glycol can be used an adhesion-promotion layer between the structure surface and the decontamination layer.

Although FIG. 3 illustrates a particular order for blocks 302-322, embodiments of the disclosed subject matter are not limited thereto. Indeed, in certain embodiments, the blocks may occur in a different order than illustrated or simultaneously with other blocks. For example, the provision of conductive material on the target surface at process block 316 may occur after the formulation of nanostructure for application at 320.

Method of Use Embodiments

Figure 4:
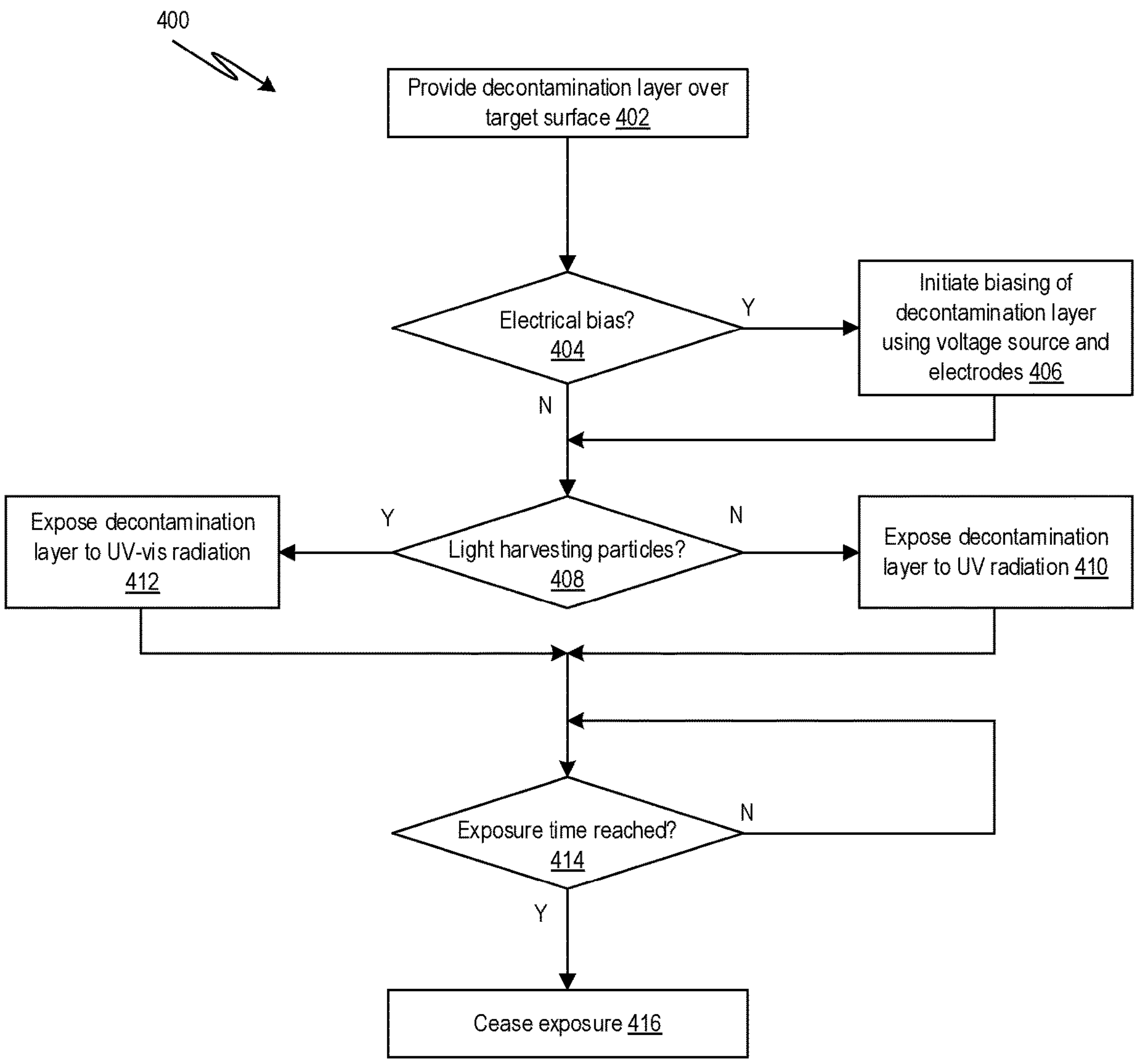
FIG. 4 is a process flow diagram to an exemplary method for the photocatalytic approach for viral decontamination using a decontamination layer, according to one or more embodiments of the disclosed subject matter.

FIG. 4 illustrates an exemplary method 400 for decontaminating a structure surface from hCoV using a nanostructured photocatalyst. The method can initiate at process block 402, where a decontamination layer is provided over a target surface of the structure. For example, the decontamination layer can be provided using the method 300 of FIG. 3 or otherwise. The decontamination layer can be provided directly on and in contact with the target surface or over the target surface with one or more intervening layers (e.g., an electrically-conductive layer, an adhesion promotion layer, etc.).

The method can proceed to decision block 404, where it is determined if an electrical bias should be applied to the decontamination layer and/or the structure. As noted above, the application of a DC electric field (or an alternating current (AC) electric field converted to DC by an appropriate converter to power supply) can enhance the photocatalytic properties of the decontamination layer. If electrical bias is desired, the method can proceed from decision block 404 to process block 406, where application of a DC electric field is initiated by an appropriate voltage source. For example, the electric field can be applied to the decontamination layer and/or the structure by electrodes in contact with the decontamination layer, the structure, and/or a layer in contact with the decontamination layer or the structure. In some embodiments, the electric field may have a magnitude less than 1 $V_{DC}$, preferably 0.1 $V_{DC}$ to 0.5 $V_{DC}$. Such electric field applications can overcome the lack of electron-hole separation in oxide materials of the nanostructure photocatalyst by suppressing recombination among charged species, electrons, and holes therein.

After process block 406, or if electrical biasing was not desired at decision block 404, the method can proceed to decision block 408, where it is determined if the decontamination layer includes light harvesting particles. If the decontamination layer includes light harvesting particles, the method can proceed to process block 412, where the decontamination layer is exposed to UV-vis radiation. As noted above, the light harvesting particles can act extend the radiation absorbance of the decontamination layer into the visible light portion of the electromagnetic spectrum. If the decontamination layer does not include light harvesting particles, the method can proceed to process block 410, where the decontamination layer is exposed to UV radiation only. In either process block 410 or 414, the source of radiation can be an existing interior lighting source, such as a halogen lamp, incandescent bulb, or fluorescent lamp, that is used to illuminate an area around or in a vicinity of structure, a source separate from any existing interior lighting source (e.g., a wavelength-selected radiation source, such as a UV lamp, laser, laser diode, or LED), or natural solar radiation.

The method can proceed to decision block 414, where it is determined if a predetermined exposure time has been reached. For example, the predetermined exposure time may be a time for irradiation that ensures all (or substantially all) hCoV in contact with the decontamination layer is inactivated. In some embodiments, the exposure time may be less than five minutes, preferably, one minute or less. If the exposure time has been reached, the method can proceed to process block 416 where the exposure (and any accompanying electrical bias) is terminated, for example, by turning off the radiation source, by blocking radiation from the radiation source, by moving the decontamination layer out of an irradiation zone, or by moving the irradiation zone away from the decontamination layer. Otherwise, if the exposure time has not been reached, the exposure (and any accompanying electrical bias) is maintained at 414.

In some embodiments, the exposure to radiation may be substantially continuous, for example, to inactivate without delay any hCoV that may come into contact with decontamination layer (for example, within one minute of initiation of contact). Such continuous radiation exposure may be especially useful where a subject would be likely to come into contact with the surface before periodic decontaminations could be applied and when exposure to the radiation would not adversely affect the subject (e.g., when existing interior illumination or natural insolation can be used as the radiation source). Alternatively or additionally, continuous radiation exposure can be used when a subject is unlikely to be exposed to the radiation, for example, when the decontamination layer is included within the housing of an air handling device.

Although FIG. 4 illustrates a particular order for blocks 402-416, embodiments of the disclosed subject matter are not limited thereto. Indeed, in certain embodiments, the blocks may occur in a different order than illustrated or simultaneously with other blocks. For example, the initiation of electrical bias at process block 406 may occur simultaneously with or after the initiation of radiation exposure 410 or 412.

Overview of Several Embodiments

In one or more first embodiments, a method can comprise exposing a human coronavirus and a decontamination layer in contact with the human coronavirus to UV radiation and/or visible light. The decontamination layer can comprise a nanostructured photocatalyst.

In the first embodiments or any other embodiment, the nanostructured photocatalyst can be formed as nanoparticles, nanotubes, nanorods, nanowires, or any combination thereof.

In the first embodiment or any other embodiment, the nanostructured photocatalyst is formed as nanotubes and the nanotubes are crystalline.

In the first embodiments or any other embodiment, the nanostructured photocatalyst can have a bandgap of 3 eV or greater.

In the first embodiments or any other embodiment, the nanostructured photocatalyst can have a bandgap of between 3 eV and 4.5 eV.

In the first embodiments or any other embodiment, the nanostructured photocatalyst comprises a metal oxide.

In the first embodiments or any other embodiment, the nanostructured photocatalyst can comprise strontium titanate ($SrTiO_3$), titanium dioxide ($TiO_2$), zinc oxide (ZnO), or any combination thereof.

In the first embodiments or any other embodiment, the nanostructured photocatalyst can comprise strontium titanate ($SrTiO_3$), titanium dioxide ($TiO_2$), and/or zinc oxide (ZnO) in any shape or form.

In the first embodiments or any other embodiment, the nanostructured photocatalyst can comprise silicon nanowires.

In the first embodiments or any other embodiment, the human coronavirus can comprise severe acute respiratory syndrome (SARS) coronavirus 2 (SARS-CoV-2), human coronavirus NL63 (hCoV-NL63), human coronavirus OC43 (hCoV-OC43), human coronavirus 229E (hCoV-229E), or any combination thereof.

In the first embodiments or any other embodiment, the decontamination layer can comprise a visible light harvesting material.

In the first embodiments or any other embodiment, the visible light harvesting material can comprise bismuth titanate.

In the first embodiments or any other embodiment, the decontamination layer can comprise an electrically-conductive additive.

In the first embodiments or any other embodiment, the electrically-conductive additive can comprise graphene, graphene oxide, graphitic carbon nitride (g-$C_3N_4$), or any combination thereof.

In the first embodiments or any other embodiment, the decontamination layer can be disposed on a first surface of a structure, with an intervening electrically-conductive layer.

In the first embodiments or any other embodiment, the electrically-conductive layer can comprise graphene, graphene oxide, graphitic carbon nitride (g-$C_3N_4$), or any combination thereof.

In the first embodiments or any other embodiment, the electrically-conductive layer can comprise a doped metal oxide film, such as a fluorine-doped tin oxide film.

In the first embodiments or any other embodiment, the method can further comprise disposing the nanostructured photocatalyst on a first surface of a structure.

In the first embodiments or any other embodiment, the structure can be a table, desk, counter, chair, bed, toilet, door, handle, wall, ceiling, flooring, or railing, and/or the first surface can be one available for touch by a subject.

In the first embodiments or any other embodiment, the structure can be an air handling device, and/or the first surface can be arranged such that the human coronaviruses in air processed by the air handling device are incident on the decontamination layer.

In the first embodiments or any other embodiment, the disposing can comprise spray painting, brush painting, roll painting, dip coating, spin coating, or any combination thereof.

In the first embodiments or any other embodiment, during or immediately prior to the disposing, components of the decontamination layer can be mixed with a binder in an emulsion.

In the first embodiments or any other embodiment, the emulsion can comprise aqueous silica or alumina sols.

In the first embodiments or any other embodiment, the method can further comprise applying an electrical bias to the decontamination layer.

In the first embodiments or any other embodiment, the applying the electrical bias can occur simultaneously with the exposing.

In the first embodiments or any other embodiment, the applied electrical bias can be less than 1 $V_{DC}$, for example, less than 0.5 $V_{DC}$.

In the first embodiments or any other embodiment, the applied electrical bias can be ±0.1-1 $V_{DC}$.

In the first embodiments or any other embodiment, the exposing can comprise using radiation emitted from an existing light source selected from a halogen lamp, incandescent bulb, or fluorescent lamp used to illuminate an area around or in a vicinity of the decontamination layer; using solar radiation; and/or using a wavelength-selected radiation source that is separate from the existing light source used to illuminate an area around or in a vicinity of the decontamination layer.

In the first embodiments or any other embodiment, the wavelength-selected radiation source can comprise a laser, laser diode, light-emitting diode, or UV lamp.

In the first embodiments or any other embodiment, a duration of the exposing can be two minutes or less, and, after the exposing, all or substantially all (e.g., 99%) of the human coronavirus on the decontamination layer has been inactivated.

In one or more second embodiments, a structure for decontamination can comprise a first surface and a decontamination layer on the first surface. The decontamination layer can comprise a nanostructured photocatalyst.

In the second embodiments or any other embodiment, the nanostructured photocatalyst can be formed as nanoparticles, nanotubes, nanorods, nanowires, or any combination thereof.

In the second embodiment or any other embodiment, the nanostructured photocatalyst is formed as nanotubes and the nanotubes are crystalline.

In the second embodiments or any other embodiment, the structure can further comprise a human coronavirus in contact with the decontamination layer.

In the second embodiments or any other embodiment, the human coronavirus can comprise severe acute respiratory syndrome (SARS) coronavirus 2 (SARS-CoV-2), human coronavirus NL63 (hCoV-NL63), human coronavirus OC43 (hCoV-OC43), human coronavirus 229E (hCoV-229E), or any combination thereof.

In the second embodiments or any other embodiment, the nanostructured photocatalyst can have a bandgap of 3 eV or greater.

In the second embodiments or any other embodiment, the nanostructured photocatalyst can have a bandgap between 3 eV and 4.5 eV.

In the second embodiments or any other embodiment, the nanostructured photocatalyst can comprise a metal oxide.

In the second embodiments or any other embodiment, the nanostructured photocatalyst can comprise strontium titanate ($SrTiO_3$), titanium dioxide ($TiO_2$), and zinc oxide (ZnO), or any combination thereof.

In the second embodiments or any other embodiment, the nanostructured photocatalyst can comprise silicon nanowires.

In the second embodiments or any other embodiment, the decontamination layer can comprise an electrically-conductive additive.

In the second embodiments or any other embodiment, the electrically-conductive additive can comprise graphene, graphene oxide, graphitic carbon nitride (g-$C_3N_4$), or any combination thereof.

In the second embodiments or any other embodiment, the decontamination layer can be disposed in contact with the first surface.

In the second embodiments or any other embodiment, the decontamination layer can be disposed on the first surface with an intervening electrically-conductive layer.

In the second embodiments or any other embodiment, the electrically-conductive layer can comprise graphene, graphene oxide, graphitic carbon nitride ($g\text{-}C_3N_4$), or any combination thereof.

In the second embodiments or any other embodiment, the electrically-conductive layer can comprise a doped metal oxide film, such as a fluorine-doped tin oxide film.

In the second embodiments or any other embodiment, the decontamination layer can be formed as a paint or coating on the first surface, and the paint or coating can include particles of silica or alumina.

In the second embodiments or any other embodiment, the structure can further comprise at least two electrodes electrically coupled to the decontamination layer and configured to apply a voltage to the decontamination layer.

In the second embodiments or any other embodiment, the structure is a table, desk, counter, chair, bed, toilet, door, handle, wall, ceiling, flooring, or railing, and/or the first surface is a surface of the structure available for touch by a subject.

In the second embodiments or any other embodiment, the structure is an air handling device, and the first surface is arranged such that any human coronaviruses in air processed by the air handling device are incident on the decontamination layer.

In one or more second embodiments, a system can comprise the structure of any of the second embodiments and an illumination source. The illumination source can generate UV radiation and/or visible light and can expose the decontamination layer of the structure to the UV radiation and/or visible light.

In the third embodiments or any other embodiment, the illumination source can comprise an existing light source selected from a halogen lamp, incandescent bulb, or fluorescent lamp used to illuminate an area around or in a vicinity of the structure.

In the third embodiments or any other embodiment, the illumination source can comprise a wavelength-selected radiation source that is separate from an existing light source used to illuminate an area around or in a vicinity of the structure.

In the third embodiments or any other embodiment, the wavelength-selected radiation source can comprise a, laser, laser diode, light emitting diode, or UV lamp.

In the third embodiments or any other embodiment, the system can further comprise one or more optical components that direct UV radiation and/or visible light from the illumination source to the decontamination layer.

In the third embodiments or any other embodiment, the system is an air handling device, and the first surface of the structure is arranged such that human coronaviruses circulating in air processed by the air handling device are incident on the decontamination layer.

EXAMPLES

Cells and viruses: Vero E6 and HEK293L cells were maintained in Dulbecco's Modified Eagle Medium (DMEM) supplemented with 10% fetal bovine serum (FBS, Atlanta Biologicals), 2 mM L-glutamine, 25 U/mL penicillin, and 25 μg/mL streptomycin. Cells were grown at 37° C. in a humidified chamber supplemented with 5% $CO_2$.

Human coronavirus: hCoV-NL63 strain, is an alphacoronavirus and belongs to the family of SARS coronaviruses. hCoV-NL63 was obtained from BEI Resources ($1.6\times10^6$ $TCID_{50}$/ml; lot 70033870, NIAID, NIH) and propagated in Vero cells by infecting the Vero cell monolayer with hCoV-NL63 for two (2) hours. Unattached virus was removed by washing followed by addition of fresh medium. After seven (7) days, virus was harvested, cell debris removed by centrifugation, and virus was quantified by quantitative real-time polymerase chain reaction (qRT-PCR). All the assays were conducted under the biosafety level 2+(BSL-2+) containment.

$TiO_2$ nanoparticles (TNP): A suspension of nanoparticles of $TiO_2$ (TNPs, 300 μg/mL) (Degussa Corporation, Piscataway, N.J.) was prepared in deionized (DI) water and vortexed. An aliquot (600 μL) of TNPs was placed on a clean UV-treated glass coverslip (to simulate a common surface) and dried at 600° C., which resulted in a semi-transparent coating. TNP-coated coverslips were stored at room temperature until further use.

$TiO_2$ nanotubes (TNT): hi some examples, $TiO_2$ nanotubes were prepared by anodization of a Ti metal foil substrate using a fluorinated solution of ethylene glycol and deionized water with an ammonium salt as the electrolyte. Further details regarding preparation of TNT and photocatalytic characteristics thereof can be found in Subramananian et al. in "$TiO_2$ nanotubes and its composites: Photocatalytic and other photo-driven applications," *J. Mater. Res.*, February 2013, 28(3): pp. 280-93, the relevant portion of which is incorporated by reference herein.

UV exposure: An aliquot of hCoV-NL63 virus (100 μL, Median Tissue Culture Infectious dose ($TCID_{50}$)) was placed on TNP-coated coverslips and uncoated coverslips (18 mm diameter) and exposed to radiation from a UV light source (USHIO Germicidal Lamp, model G30T8) that generated UV-C light ($\lambda$=254 nm, 99V, 30 W, 0.355 A). The UV light source was placed 76 cm from the bottom of the wells containing coverslips and emitted 2900 $\mu W/cm^2$. An aliquot was collected and used for total RNA extraction or applied on permissive human embryonic kidney cell (HEK293L) monolayer for the detection of infectious virus.

Virus infectivity assay: HEK293L cell monolayer was inoculated with hCoV-NL63 virus aliquot for two (2) hours at 37° C., 5% $CO_2$. The cells were washed to remove the unbound virus followed by addition of fresh medium. At forty-eight (48) hours after initial infection, the monolayers were harvested and used for total RNA extraction.

RNA extraction and qPCR: Total RNA was extracted using Trizol reagent (Invitrogen, Carlsbad, CA) according to the manufacturer's recommendation. An aliquot of RNA (1 μg) was used for synthesizing the cDNA (Superscript kit; Invitrogen, Carlsbad, CA). cDNA (2 μL) was used for the relative quantification of viral genome RNA in a qPCR assay (ThermoFisher Scientific, Waltham, MA). Primers used were NL63-SF 5'-GTGCCATGACCGCTGTTAAT-3', SEQ ID NO: 1; and NL63-SR 5'-GCGGACGAACAGGAATCAAA-3', SEQ ID NO: 2. For generating a standard curve to estimate the viral copies, 100 μl of NL63 stock (BEI Resources) with known amounts of hCoV-NL63 was used for total RNA extraction and cDNA synthesis. An aliquot (2 μl) of hCoV-NL63 cDNA used for qRT-PCR was equivalent to 320 copies of hCoV-NL63 ($1.6\times10^6$ $TCID_{50}$/ml; lot 70033870, NIAID, NIH). A ten-fold dilution of hCoV-NL63 virus (BEI Resources) was generated and used as a standard curve.

Immunofluorescence analysis: Cells were fixed using a ratio of methanol to acetone of 3:1, and stored at −80° C. until used. Slides were permeabilized with 0.1% Triton X-100 for 30 minutes, washed (3×) and blocked (3% normal donkey serum, 0.5% BSA) for one (1) hour at room temperature. Cell monolayers were washed again (3×) and incubated with rabbit anti-CoV antibody (1:200; BEI Resources, NIAID, NIH) for one (1) hour at room temperature, followed by incubation with goat anti-rabbit Alexa Fluor 488 (1:5000; Molecular Probe, Carlsbad, CA) and secondary antibody for one (1) hour at room temperature in the dark. Finally, the nuclei were stained with TOPRO-3 (ThermoFisher, Walthman, MA). Coverslips were mounted on the glass slides using antifade and the slides were examined using a confocal laser-scanning microscope (Carl Zeiss LSM 780).

Statistical analysis: Statistical analyses were performed using Prism 7.0 software (Graphpad Inc.) and the p-values were calculated using two-tailed t-tests.

Example 1—UV Versus UV+Titanium Oxide Nanoparticles (TNPs)

Figure 6:
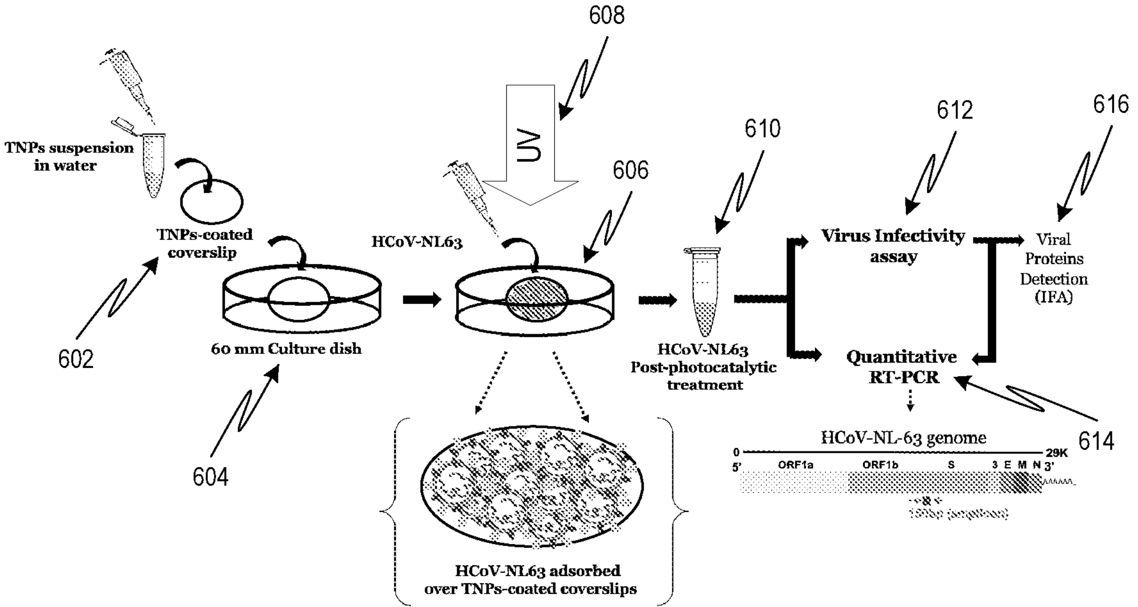
FIG. 6 illustrates an experimental setup used to evaluate inactivation of human coronavirus NL-63 (hCoV-NL63) using UV irradiation in combination with a photocatalytic decontamination layer prepared on a glass cover slip.

In order to test the efficacy of titanium oxide nanoparticles (TNPs) in accelerating the inactivation of hCoV-NL63 upon exposure to UV radiation, the experimental setup illustrated in FIG. 6 was used. For the experiments with UV exposure in combination with a TNP layer, a suspension of TNPs was prepared and deposited on glass coverslips as a semitransparent film, as shown at stage 602 in FIG. 6. The TNPs were prepared as a suspension in water and were subsequently deposited on the glass coverslips by drying at 60° C. for four (4) to five (5) hours. TNP-coated coverslips were then placed in the center of a 60 mm culture dish, as shown at stage 604 in FIG. 6. For the experiments with UV exposure alone, uncoated glass coverslips were used. The coverslips were placed inside respective wells of a 12-well plate.

An aliquot of hCoV-NL63 virus (100 μl suspension) was applied on top of the coverslips in each well, as shown at stage 606 in FIG. 6. The virus and coverslip were then exposed to UV radiation 608 for selected time durations (e.g., 0, 1, 5, 10, and 30 minutes) within a BSL-2 biological safety cabinet, after which the inactivated virus was collected at stage 610 and evaluated for the viral genomic RNA stability via quantitative RT-PCR at stage 614, virus infectivity at stage 612, and detection of viral proteins via immunofluorescence assay (IFA) at stage 616, all with reference to FIG. 6. In particular, the UV-exposed virus was collected for evaluation of virus inactivation by direct genomic RNA quantitation (qRT-PCR) and infectivity assay on an HEK293L monolayer. Total RNA was extracted and quantified for genome RNA fragmentation due to cross-linking and oxidative damage by UV exposure. hCoV-NL63 viral copies were calculated using standard curve generated on the basis of serial dilutions of known hCoV-NL63 genomic RNA.

Figures 7A, 7B, 8, 9:
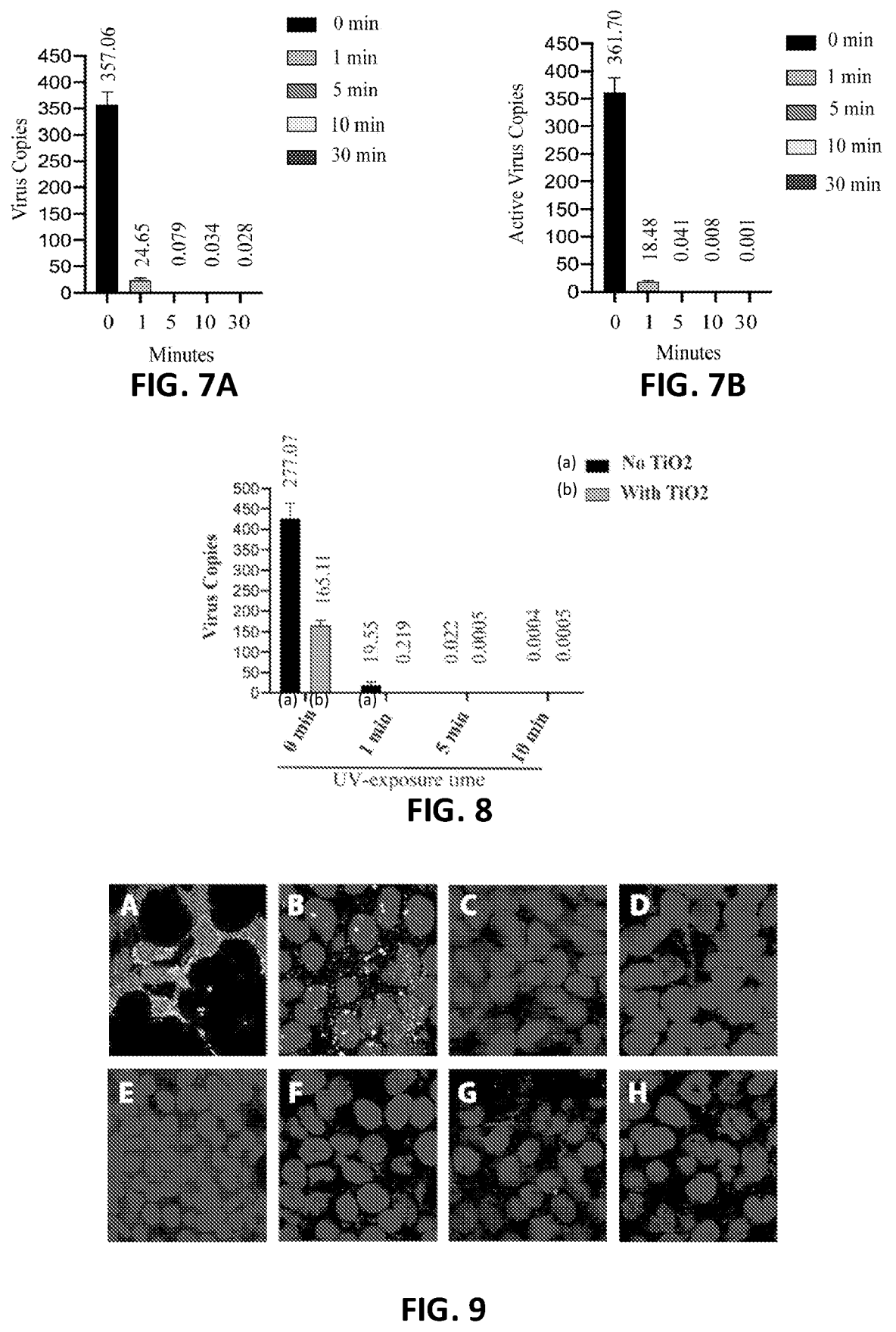

For the uncoated coverslips (i.e., UV exposure alone), the calculated copies of the viral genomic RNA declined with increasing UV-exposure time, as reflected in the data of FIG. 7A. There was also an efficient reduction in the number of intact viral genomic RNA at one-minute exposure to the UV-light; however, there were still intact copies of hCoV-NL63 at least in the region (spike protein), used for the detection in of qRT-PCR assay. In addition, increasing the exposure time to greater than five minutes resulted in almost complete degradation of the hCoV-NL63 genome, with exposures around five minutes resulting in limited intact genomes. The results of FIG. 7A thus confirm that efficient inactivation of viruses is possible through UV exposure alone.

To further detect whether the UV-exposure alone reduced the infectivity of hCoV-NL63 virus (in addition to the intactness of genomic RNA determined by the qRT-PCR), HEK293L cell monolayers were inoculated with the UV-treated hCoV-NL63 for two hours to facilitate attachment and infection. The total RNA collected forty-eight hours post infection (hpi) was used for the detection of hCoV-NL63 genomic RNA, which indirectly measured the amounts of infectious virus. As reflected in the data of FIG. 7B, the infectious viruses were reduced to almost background levels when subjected to UV exposures of at least five minutes. However, as shown in FIG. 7B, for exposures of one minute, infectious viral particles of hCoV-NL63 were still detectable, although significantly reduced as compared to no UV exposure. This suggests that UV exposures of one minute or less (alone) do not completely inactivate the virus and thus would not provide sufficient decontamination of the surface.

For the coated coverslips (i.e., UV exposure in combination with TNP decontamination layer), the viral copies quantified through RT-qPCR for viral genome fragmentation showed a significant reduction in the number of detected copies of hCoV-NL63 as compared to the uncoated coverslips (i.e., UV exposure alone), as reflected in the data of FIG. 8. Indeed, for exposure times as short as one minute, the coated coverslips experienced a reduction in hCoV-NL63 copies to almost background levels. Note that the variation in FIG. 8 for the number of hCoV-NL63 detected for the coated and uncoated coverslips at 0 minutes of UV-exposure (i.e., control) is likely a product of the recovery rate of the virus from the coverslips.

To correlate virus inactivation with infectivity, viruses recovered after UV-exposure were added onto the monolayer of HEK293L cells. The remaining infectious viral copies following UV-exposure were determined by localizing hCoV-NL63 viral protein, which is produced following the replication of live virus through their localization (i.e., via immunofluorescence assay). In panel A of FIG. 9, the replication hCoV-NL63 in HEK293L cells infected with untreated virus is detected by green fluorescent proteins dots. Specificity of viral replication and protein detection was confirmed by the lack of these protein in uninfected HEK293L cells in panel E of FIG. 9. The images of FIG. 9 further illustrate that complete elimination of live virus can have achieved by UV exposures of one minute in the presence of TNPs (panel F), while UV exposures without TNPs (panel B) for the same exposure time are insufficient to eliminate the live virus. Longer UV exposure times completely inactivated the virus, as indicated by the lack of protein imaged in panels C, D, G, and H of FIG. 9. These data thus confirm that a decontamination layer of TNPs can enhance the inactivation efficiency of UV light and can effectively degrade hCoV-NL63 virus thereby rendering it non-infectious.

Example 2—UV+TNP Versus UV+Titanium Oxide Nanotubes (TNT)

In order to compare the efficacy of titanium oxide nanotubes (TNTs) to that of titanium oxide nanoparticles (TNPs) in accelerating the inactivation of hCoV-NL63 upon exposure to UV radiation, the experimental setup illustrated in FIG. 6 was again used. For the experiments with UV exposure in combination with a TNT layer, the TNT was prepared on the coverslip using anodization. The TNP-coated coverslips and uncoated coverslips were otherwise prepared as described above. Each coverslip was placed inside a culture dish, as illustrated in FIG. 6. An aliquot of hCoV-NL63 virus (100 μl suspension) was applied on top of each coverslip, and UV exposure and subsequent qRT-PCR and infectivity assays were performed in a manner similar to that described above in Example 1.

Figure 10:
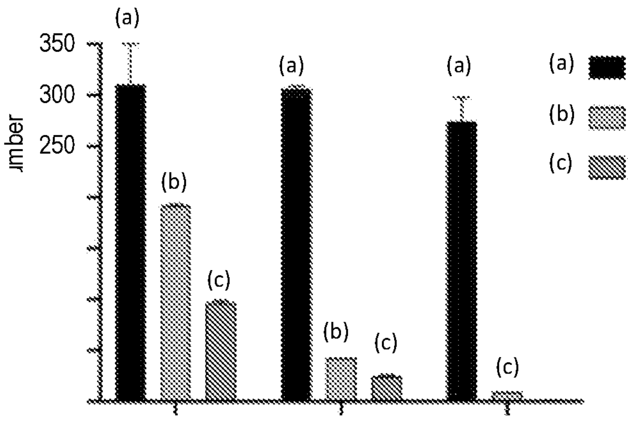
FIG. 10 is a graph of active copies of hCoV-NL63 collected from the setup of FIG. 6 after different UV radiation exposure times (i) without any decontamination layer, (ii) with a decontamination layer of TNPs and (iii) a decontamination layer of $TiO_2$ nanotubes (TNT).
Figure 11:
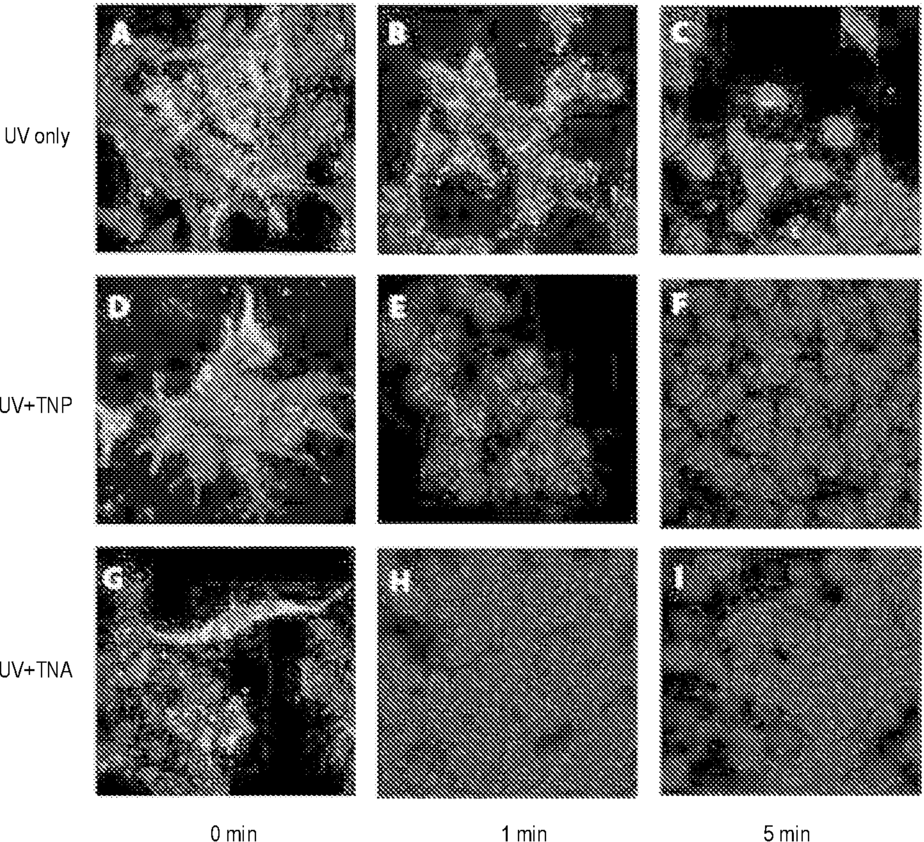
FIG. 11 shows immunofluorescence assay images of a monolayer of HEK293L cells infected by copies of hCoV-NL63 for different decontamination parameters, with panels A-C showing infection by hCoV-NL63 after 0, 1, and 5 minute exposures to UV radiation, respectively, without any decontamination layer; panels D-F showing infection by hCoV-NL63 after 0, 1, and 5 minutes exposures to UV radiation, respectively, with a decontamination layer of TNPs; and panels G-I showing infection by hCoV-NL63 after 0, 1, and 5 minutes exposures to UV radiation, respectively, with a decontamination layer of TNT.

As reflected in the RT-qPCR data of FIG. 10 and the IFA data of FIG. 11, the provision of a decontamination layer (whether TNT or TNP) significantly enhances the efficacy of the UV exposure to inactivate hCoV-NL63. Moreover, the use of TNT for the decontamination layer provides even greater enhancement than use of TNP. Indeed, complete elimination of the virus can be achieved with a five minute UV-exposure using TNT as compared to either TNP or UV alone. Further optimization of the construction and/or composition of the decontamination layer (e.g., additives or light harvesting materials) and/or irradiation wavelengths, and/or provision of an external electrical bias to the decontamination layer, can further reduce the time needed for sufficient inactivation, thereby resulting in effective decontamination of the surface in one minute or less.

Examples 1 and 2 thus illustrate that a decontamination layer comprised of nanostructured $TiO_2$ can work synergistically with UV exposure to quickly and efficiently inactive human coronavirus from a surface. Although the data above are presented for hCoV-NL63 instead of SARS-CoV-2, hCoV-NL63 is recognized by the American Society for Testing and Materials (ASTM) as a recommended testing surrogate for SARS-CoV-2. Indeed, since both hCoV-NL63 and SARS-CoV-2 both cause respiratory diseases and have similar virion structures, it is expected that the inactivation parameters will be the same, or at least substantially similar, for both viruses.

Example 3—Bismuth Titanate Nanoparticles as Light Harvesting Material

As described above, additives such as bismuth titanate can be added to the decontamination layer to enhance photocatalytic properties. To demonstrate the enhancement, TNT combined with bismuth titanate ($Bi_{12}TiO_{20}$) nanoparticles (BTN) were prepared as described above and compared against TNT alone under UV-visible and visible light exposures. As shown by the results in Table 1, the addition of BTN to the TNT boosted photocurrent, which is a measure of photocatalytic activity. It also enhanced overall light absorbance by shifting the onset absorbance wavelength toward the visible spectrum, thereby allowing visible wavelengths to contribute to photocatalysis. The addition of BTN or other light harvesting materials can thus allow visible light sources (e.g., existing interior lighting) to be used to provide periodic or continuous exposure of the nanostructured photocatalyst for decontamination.

TABLE 1

Bismuth Titanate Nanoparticles as Light Harvesting Material

| Layer Composition | $\lambda_{onset}$ (nm) | Photocurrent Density - J UV + Visible | Photocurrent Density - J Visible |
|---|---|---|---|
| TNT only | 330 | 1.6 mA/cm$^2$ | 0.7 mA/cm$^2$ |
| TNT + $Bi_{12}TiO_{20}$ | 380 | 2.1 mA/cm$^2$ | 0.8 mA/cm$^2$ |

Example 4—Application of Electrical Field

As described above, the lack of electron-hole separation in certain materials of the nanostructured photocatalyst can be overcome by applying a DC electric field to the decontamination layer and/or the structure, thereby enhancing the photocatalytic properties of the decontamination layer. To demonstrate the enhancement, titanium dioxide nanotubes (TNT) were provided on different substrates (metal mesh or metal coil) and used to photocatalytically degrade a dye (methylene blue) under UV exposure, during which a DC voltage is applied across the TNT layer. As shown by the results in Table 2, the application of an electrical field significantly enhances the photocatalytic capability of the TNTs, as evidenced by the increasing dye degradation with applied voltage. The enhancement can be mainly attributed to the suppression of recombination among charged species, electrons, and holes in the oxide material. Thus, with application of voltage as little as 0.1-0.4 $V_{DC}$, the degradation of dye by the TNTs can be enhanced by a factor of ~2-3.

TABLE 2

Effect of DC bias on Degradation of Dye

| Composition | Dye Degradation for Applied Bias: No Bias | +0.1 $V_{DC}$ | +0.4 $V_{DC}$ |
|---|---|---|---|
| Metal-mesh/TNT | 4.5% | 7.6% | 12.1% |
| Metal-coil/TNT | 6.4% | 10.4% | 15.4% |

Example 5—Reduced Graphene Oxide as Electrically Conductive Additive

As described above, electrically-conductive materials can be added to the decontamination layer and/or added as an intervening layer between the decontamination layer and the structure surface to improve radiation absorption and/or the electrical conductivity thereof, for example, to assist in the application of an external DC field. To demonstrate the improvement, a reduced graphene oxide (RGO) layer was prepared as described above and coated on a non-conductive glass substrate. TNTs were provided on this RGO layer as well as directly on a separate non-conductive glass substrate, and both substrates were exposed to UV radiation. As shown by the results in Table 3, the addition of RGO decreased the electrical resistance of the substrate with TNT layer and significantly improved the resulting photocurrent. Thus, a non-conductive surface can be made conductive, which can allow application of the DC fields described above in Example 4.

TABLE 3

Reduced Graphene Oxide as Electrically Conductive Material

| Composition | Resistance (kΩ) | Photocurrent Density - J |
|---|---|---|
| Glass/TNT | 2.59 | 0.3 μA/cm$^2$ |
| Glass/RGO/TNT | 0.9 | 1.2 μA/cm$^2$ |

Example 6—Zinc Oxide Nanotubes

Zinc oxide (ZnO) has characteristics similar to that of titanium oxide ($TiO_2$), in that it has a similarly large bandgap (e.g., ~3.2 eV), can be prepared as 0-D and 1-D nanostructures, and has photocatalytic properties. ZnO nanotubes (ZNA) were fabricated and used to photocatalytically degrade a dye (methylene blue) under UV exposure. As shown in the Table 4, the ZNA offers photocurrent densities similar to that of TNT. Moreover, the ZNA offers significant photocatalytic capability, as exhibited by the substantial dye degradation. Photocatalytic capability can be further enhanced by including a conductive additive (e.g., RGO) in the ZNA layer, as indicated by the data in Table 4. Accordingly, ZnO nanostructures are expected to perform similarly with respect to viral decontamination as $TiO_2$ nanostructures and can be substituted for $TiO_2$ in any of the above described examples or embodiments. ZnO nanostructures may also be cheaper to fabricate than $TiO_2$ nanostructures, and offer fluorescence properties that may be leveraged for additional uses (e.g., sensing).

TABLE 4

Performance of ZNA in Degradation of Dye

| Layer Composition | Photocurrent Density - J | Dye Degradation |
|---|---|---|
| ZNA only | 1.5 mA/cm$^2$ | 80% |
| ZNA + RGO | 2 mA/cm$^2$ | 95% |

Example 7—Evaluation of Photo-Induced Inactivation by TNTs and TNPs

Figure 13:
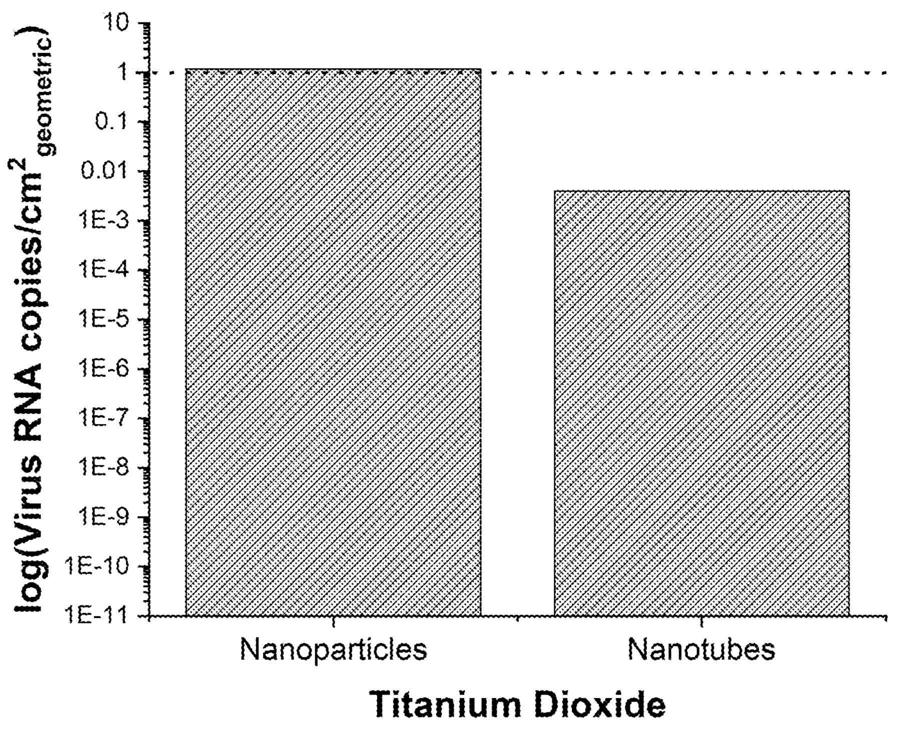
FIG. 13 is a graph of log(virus RNA copies/$cm^2$) as a function of titanium dioxide geometry; the samples were illuminated for 30 seconds with a light intensity of 2900 $\mu W/cm^2$.

In this example, the effect of catalyst shape was evaluated for particular titanium dioxide catalyst embodiments. Nanotubes of titanium dioxide and nanoparticles of titanium dioxide were evaluated. The TNTs were anodized at 40V for 60 minutes and annealed at 450° C. The TNPs were deposited on a glass cover slip. The ability of the nanostructures was evaluated by exposing a sample comprising hCoV-OC43 virus particles to the differently-shaped nanostructures. The hCoV-OC43 virus particles had diameters ranging from 80-120 nm and were enveloped with club-like projections of a spike protein. The sample was then illuminated using a light intensity of 2900 μW/cm$^2$ for 30 seconds. Results are shown in FIG. 13, wherein a value of less than 1 on the Y axis indicates complete inactivation of the virus. In this particular example, the TNTs were found to exhibit increased inactivation relative to the TNPs.

Example 8—Evaluation of Effect of Annealing on Photocatalytic Inactivation

Figure 12A:
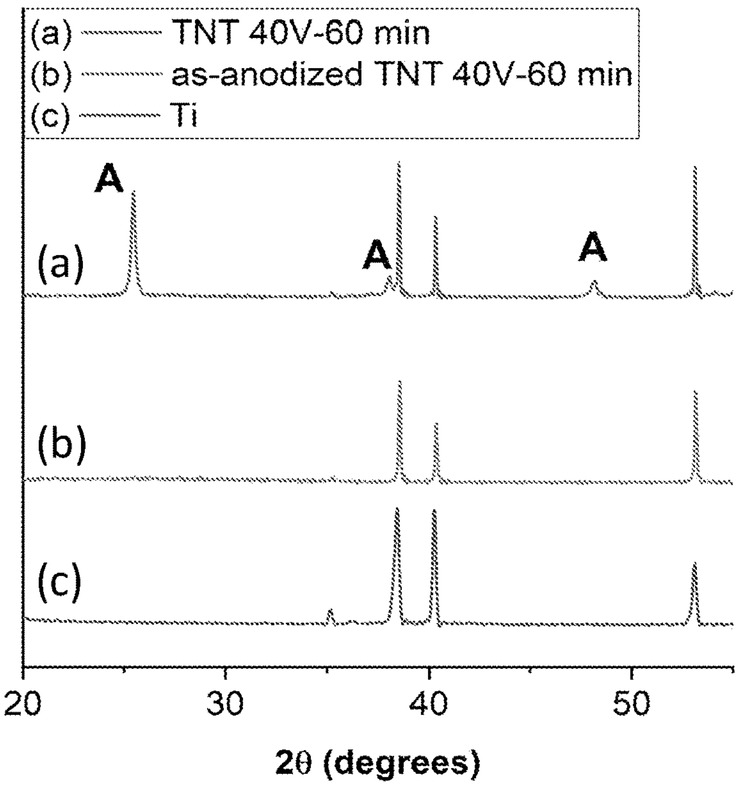
FIG. 12A shows X-ray diffraction (XRD) spectra of TNTs showing that anatase phase formation and crystallinity can increase after annealing the anodized TNTs over a temperatures ranging from 300° C. to 600° C.
Figure 12B:
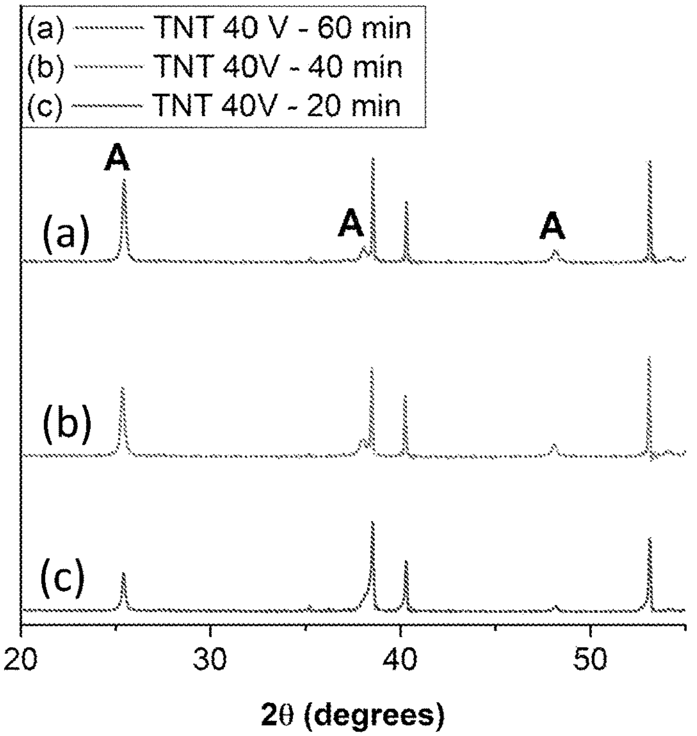
FIG. 12B shows XRD spectra of TNTs after being anodized for different time periods at a voltage of 40V, wherein anatase phase and crystallinity increase with increased anodization time.
Figure 14:
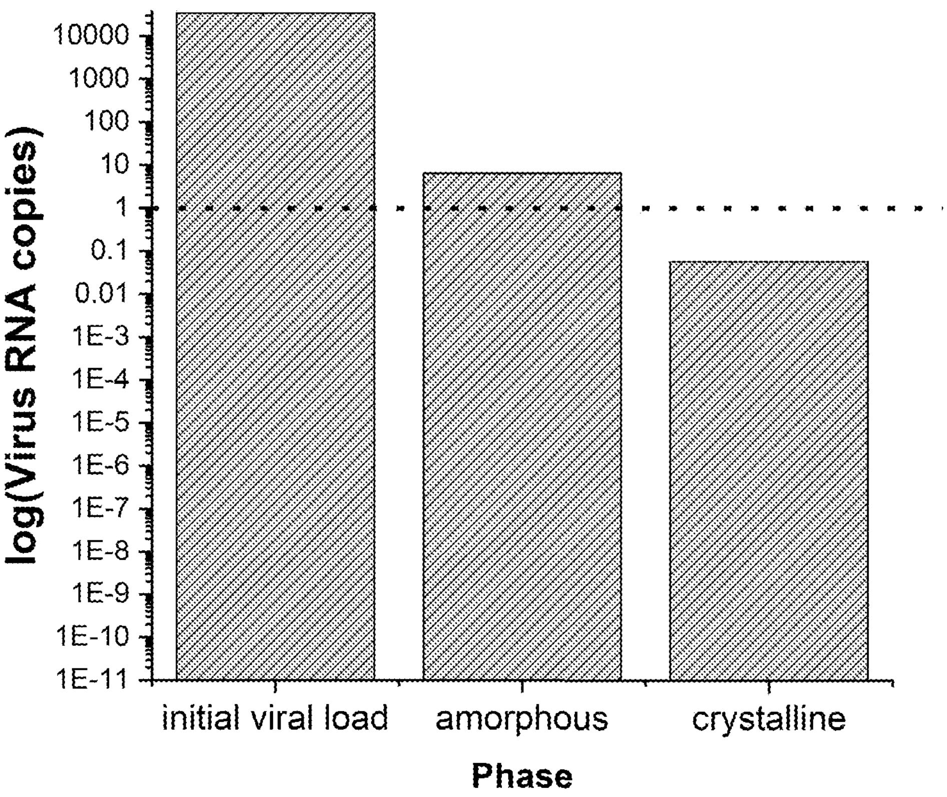
FIG. 14 is a graph of log(virus RNA copies) as a function of the phase of the TNTs, specifically amorphous and crystalline phases; the initial viral load is illustrated for comparison and it can be seen that the crystalline phase of the TNTs can facilitate improved inactivation.

In this example, the effect of annealing on photocatalytic inactivation was evaluated for TNTs. Anodized and annealed TNTs were evaluated. For both samples, the TNTs were anodized at 40V for 60 minutes. One sample was further annealed at 450° C.±5° C. to provide crystalline-phase TNTs. The unannealed sample was amorphous. The hCoV-OC43 virus particles of Example 7 were used and were exposed to the annealed and unannealed TNTs. The samples were then illuminated using a light intensity of 2900 μW/cm$^2$ for 30 seconds. Results are shown in FIG. 14, wherein a value of less than 1 on the Y axis indicates complete inactivation of the virus. In this particular example, the annealed TNTs were found to exhibit increased inactivation relative to the unannealed TNTs. FIGS. 12A and 12B show XRD spectra that show the effect of annealing (FIG. 12A) and increasing anodization time (FIG. 12B) on crystallinity of the TNTs.

Example 9—Evaluation of Virus Inactivation at Different UV Exposure Times

Figure 15:
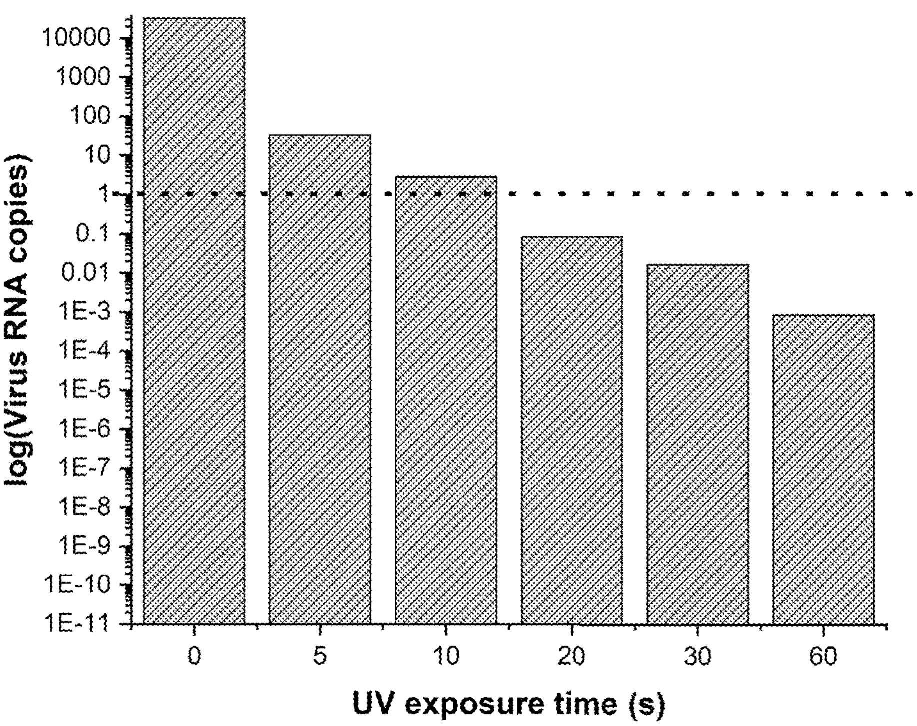
FIG. 15 is a graph of log(virus RNA copies) as a function of UV exposure time (in seconds).

In this example, the effect of UV exposure time on photocatalytic inactivation was evaluated for TNTs. Anodized and annealed TNTs were evaluated. The TNTs were anodized at 40V for 60 minutes and annealed at 450° C.±5° C. The hCoV-OC43 virus particles of Example 7 were used and were exposed to the TNTs. The samples were then illuminated using a light intensity of 2900 μW/cm$^2$ for time periods ranging from 0 seconds to 60 seconds, including 5 seconds, 10 seconds, 20 seconds, 30 seconds, and 60 seconds. Results are shown in FIG. 15, wherein a value of less than 1 on the Y axis indicates complete inactivation of the virus. In this particular example, a minimum exposure time of 20 seconds was shown to be effective in inactivating the virus.

Example 10—Evaluation of TNT Length on Virus Inactivation

Figure 16:
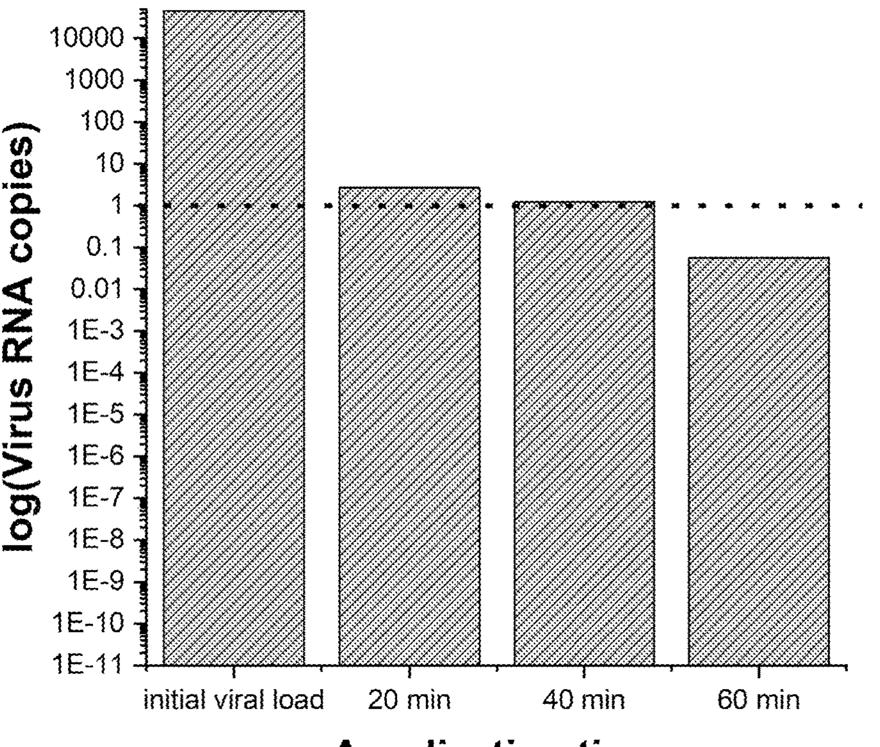
FIG. 16 is a graph of log(virus RNA copies) as a function of TNT length (as influenced by anodization time); the initial viral load is illustrated for comparison and it can be seen that longer anodization times (which provides TNTs with increased lengths) can facilitate improved inactivation.

In this example, the effect of TNT length on photocatalytic inactivation was evaluated for TNTs. Anodized and annealed TNTs were evaluated. The TNTs were anodized at 40V for different time periods ranging from 20 minutes to 60 minutes (such as 20 minutes, 40 minutes, and 60 minutes) and were annealed at 450° C.±5° C. The hCoV-OC43 virus particles of Example 7 were used and were exposed to the TNTs. Anodizing the TNTs for longer time periods facilitated increasing the length of the nanotubes. Results for this example are shown in FIG. 16, wherein a value of less than 1 on the Y axis indicates complete inactivation of the virus. In this particular example, longer anodization time periods increased nanotube length and increased the surface area for photocatalytic inactivation.

Example 11—Evaluation of Effect of TNT Diameter on Virus Inactivation

Figure 17:
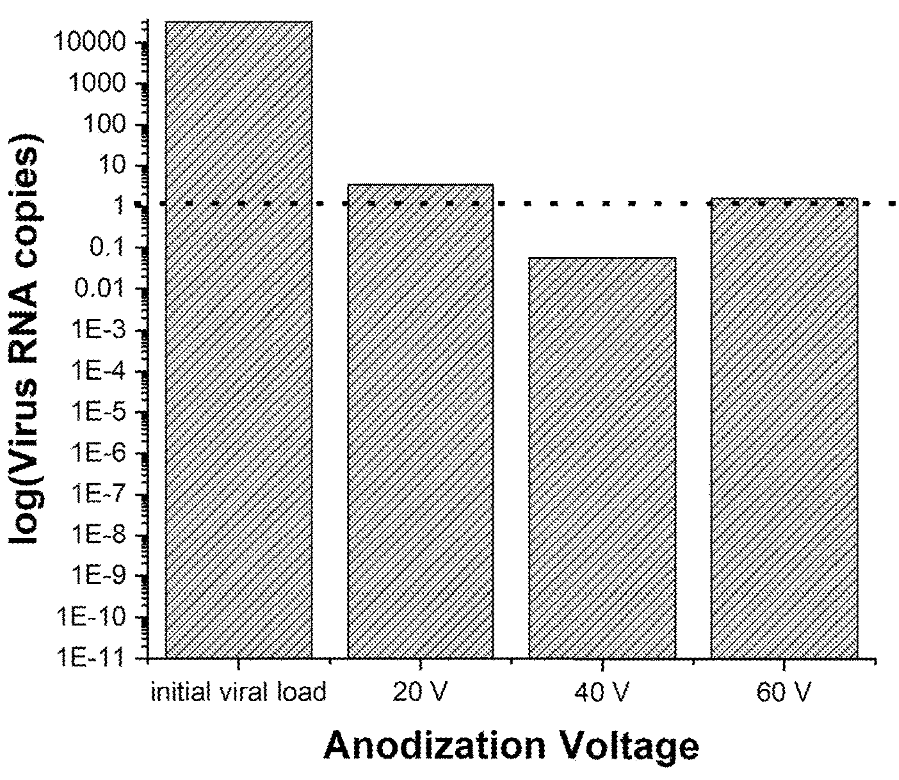
FIG. 17 is a graph of log(virus RNA copies) as a function of anodization voltage.

In this example, the effect of TNT diameter on photocatalytic inactivation was evaluated for TNTs. Anodized and annealed TNTs were evaluated. The TNTs were anodized at different voltages ranging from 20V to 60V (in particular 20V, 40V, and 60V) for 60 minutes and were annealed at 450° C.±5° C. The hCoV-OC43 virus particles of Example 7 were used and were exposed to the TNTs. Anodizing the TNTs at different voltages can facilitate modifying the diameter of the nanotubes. Results for this example are shown in FIG. 17, wherein a value of less than 1 on the Y axis indicates complete inactivation of the virus.

Example 12—Evaluation of Cyclic Stability of TNTs

Figure 18:
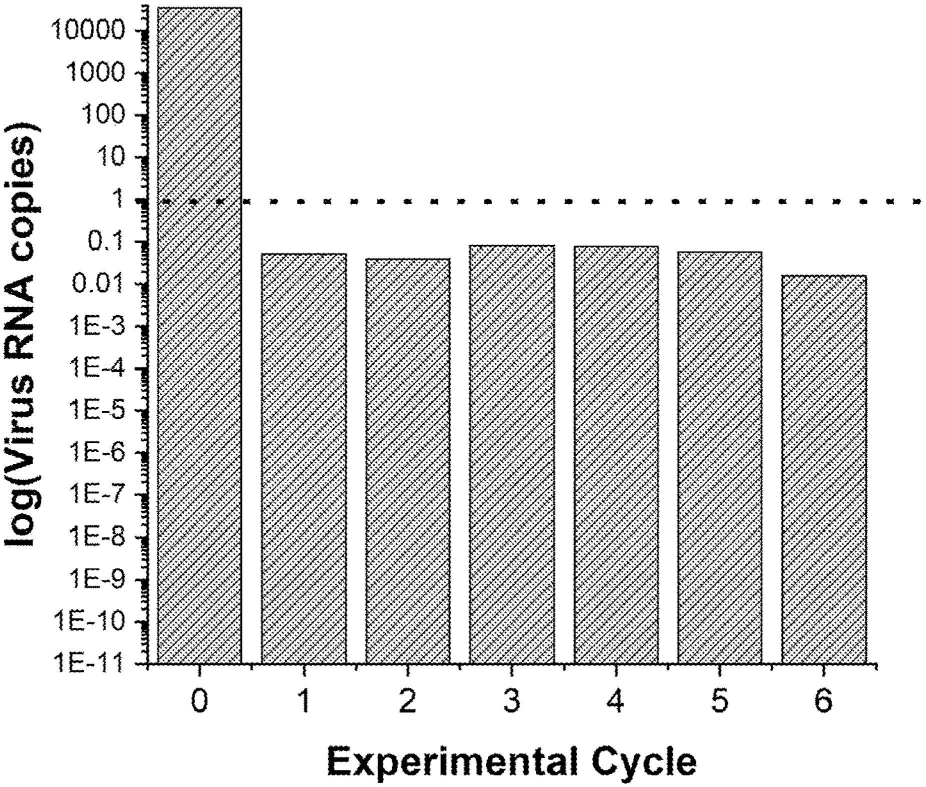
FIG. 18 is a graph of log(virus RNA copies) as a function of the number of cycles during which the viral load is exposed to TNTs.

In this example, the stability of TNTs as a function of photocatalytic cycles was evaluated. Anodized and annealed TNTs were evaluated. The TNTs were anodized at 40V for 60 minutes and were annealed at 450° C.±5° C. The hCoV-OC43 virus particles of Example 7 were used and were exposed to the TNTs. The number of cycles ranged from 0 to 6; however, the present disclosure is not limited to this number of cycles and can include other cycle numbers ranging from 1 to 20 or more, such as 1 to 10, or 1 to 9, or 1 to 8, or 1 to 7). The TNTs were cleaned with 70% ethanol after each cycle, followed by drying. Results for this example are shown in FIG. 18, wherein a value of less than 1 on the Y axis indicates complete inactivation of the virus. As can be seen, the TNTs are robust and demonstrated little to no loss of activity for at least 6 cycles.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A decontamination system, comprising:

a first surface;

a decontamination layer, wherein the decontamination layer disposed on the first surface, wherein the decontamination layer comprises a nanostructured photocatalyst, wherein the nanostructured photocatalyst comprises: nanoparticles, nanotubes, nanorods, nanowires, or any combination thereof, wherein the nanostructured photocatalyst comprises: a metal oxide selected from strontium titanate ($SrTiO_3$), titanium dioxide ($TiO_2$), zinc oxide (ZnO), or any combination thereof, wherein the nanostructured photocatalyst has a bandgap of 3 eV or greater, wherein the decontamination layer comprises an electrically-conductive additive, and wherein the electrically-conductive additive comprises: graphene, graphene oxide, graphitic carbon nitride (g-$C_3N_4$), or any combination thereof;

a voltage source, wherein the voltage source is electrically coupled to the decontamination layer;

an interdigitated electrode array, wherein the interdigitated electrode array is electrically coupled to the voltage source, wherein the interdigitated electrode array comprises a positive electrode with a plurality of first fingers extending therefrom and a negative electrode with a plurality of second fingers extending therefrom, wherein the first fingers and the second fingers are alternately disposed with each other, such that each first finger is disposed between a pair of adjacent second fingers, except for the fingers at an end of the array, wherein the nanostructured photocatalyst is disposed within gaps between the fingers and electrodes, and wherein the interdigitated electrode is disposed on the decontamination layer, under the decontamination layer, or within the decontamination laver; and an illumination source, wherein the illumination source is selected from the list: a halogen lamp, incandescent bulb, laser, laser diode, light emitting diode, UV lamp, and fluorescent lamp, wherein the illumination source generates UV radiation or visible light, and wherein the illumination source is configured to irradiate the decontamination layer, and wherein the first surface of the decontamination system is configured such that human coronaviruses circulating in air processed by the decontamination system are incident on the decontamination layer.

2. The decontamination system of claim 1, further comprising a human coronavirus in contact with the decontamination layer, wherein the human coronavirus comprises severe acute respiratory syndrome (SARS) coronavirus 2 (SARS-COV-2), human coronavirus NL63 (HCoV-NL63), human coronavirus OC43 (HCoV-OC43), human coronavirus 229E (HCoV-229E), or any combination thereof.

3. The decontamination system of claim 1, wherein the nanostructured photocatalyst comprises crystalline nanotubes or silicon nanowires.

4. The decontamination system of claim 1, wherein the voltage source a direct current voltage source.

5. The decontamination system of claim 1, wherein the decontamination layer includes particles of silica or alumina.

6. The decontamination system of claim 4, wherein the decontamination layer has an electrical bias of less than 0.5 $V_{DC}$.

7. The decontamination system of claim 4, wherein the interdigitated electrode is disposed on the decontamination layer.

8. The decontamination system of claim 4, wherein the interdigitated electrode is disposed under the decontamination layer.

9. The decontamination system of claim 4, wherein the interdigitated electrode is positioned within the decontamination layer.

* * * * *

```
SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: NL63-SF

<400> SEQUENCE: 1

gtgccatgac cgctgttaat                                                20


<210> SEQ ID NO 2
<211> LENGTH: 20
<212> TYPE: DNA
<213> ORGANISM: Artificial Sequence
<220> FEATURE:
<223> OTHER INFORMATION: NL63-SR

<400> SEQUENCE: 2

gcggacgaac aggaatcaaa                                                20
```